US007122194B2

(12) United States Patent
Johnson et al.

(10) Patent No.: US 7,122,194 B2
(45) Date of Patent: Oct. 17, 2006

(54) VACCINE COMPOSITIONS COMPRISING *STREPTOCOCCUS PNEUMONIAE* POLYPEPTIDES HAVING SELECTED STRUCTURAL MOTIFS

(75) Inventors: Leslie S. Johnson, Darnestown, MD (US); John E. Adamou, New Milford, CT (US)

(73) Assignee: MedImmune, Inc., Gaithersburg, MD (US)

( * ) Notice: Subject to any disclaimer, the term of this patent is extended or adjusted under 35 U.S.C. 154(b) by 527 days.

(21) Appl. No.: 10/412,850

(22) Filed: Apr. 14, 2003

(65) Prior Publication Data

US 2004/0001836 A1    Jan. 1, 2004

Related U.S. Application Data

(62) Division of application No. 09/468,656, filed on Dec. 21, 1999, now Pat. No. 6,582,706.

(60) Provisional application No. 60/113,048, filed on Dec. 21, 1998.

(51) Int. Cl.
*A61K 39/02* (2006.01)
*A61K 49/00* (2006.01)

(52) U.S. Cl. .................. 424/234.1; 424/9.2; 424/184.1; 424/190.1; 424/237.1; 424/244.1; 435/7.34; 530/350

(58) Field of Classification Search ............. 424/184.1, 424/185.1, 190.1, 237.1, 244.1, 9.2, 234.1; 435/69.1, 36.1, 7.34; 514/44; 530/350; 536/23.1, 23.7
See application file for complete search history.

(56) References Cited

U.S. PATENT DOCUMENTS 6,042,838 A * 3/2000 Briles et al. ............. 424/244.1

| 6,420,135 | B1 | 7/2002 | Kunsch et al. |
| 6,699,703 | B1 | 3/2004 | Doucette-Stamm et al. |

FOREIGN PATENT DOCUMENTS

| WO | WO 95/06732 | 3/1995 |
| WO | WO 97/48417 | 6/1996 |
| WO | WO 97/41151 | 11/1997 |
| WO | WO 98/18931 | 5/1998 |
| WO | WO 98/18930 | * 7/1998 |
| WO | WO 99/15675 | 4/1999 |
| WO | WO 00/17370 | 3/2000 |
| WO | WO 00/39299 | 6/2000 |

OTHER PUBLICATIONS

Abaza et al. J. Protein Chemistry vol. 11, No. 5, pp. 433-444 (1992).
Cundell et al. Microbial Pathogenesis vol. 17, pp. 361-374 (1994).
Cundell et al. Nature vol. 377, pp. 435-438 (1995).
Idanpaan-Heikkila et al. J. Infectious Dis. vol. 176, pp. 704-712 (1997).
Lupas et al. Science vol. 252, pp. 1162-1164 (1991).
Paul, W.E., in Fundamentals of Immunology, Raven Press, New York, NY (1993) 3rd Ed. p. 251.
Riffkin et al. Gene vol. 167, pp. 279-283 (1995).
Ristori et al. FASEB Journal, vol. 14, pp. 431-438 (2000).
Tuomanen et al., New Engl. J. Med., vol. 332, pp. 1280-1284 (1995).

* cited by examiner

*Primary Examiner*—Bruce Campell
(74) *Attorney, Agent, or Firm*—Elliot M. Olstein; Alan J. Grant

(57) ABSTRACT

A vaccine composition is disclosed that comprises polypeptides and fragments of polypeptides containing histidine triad residues or coiled-coil regions, some of which polypeptides or fragments lie between 80 and 680 residues in length. Also disclosed are processes for preventing infection caused by *S. pneumoniae* comprising administering of vaccine compositions.

10 Claims, 17 Drawing Sheets

A. Strain SJ2 (serotype 6B)

B. Strain EF6796 (serotype 6A)

PhtA

PhtA N-terminal

PhtA C-terminal

Figure 6(a)

```
          C S Y E L G R H Q A G Q X K K E S N R V S Y I D G D Q A G Q K A E N L T P D E V S K R E G I N A E Q  Majority
                    10                  20                  30                  40                  50
  1     C S Y E L G R H Q A G Q V K K E S N R V S Y I D G D Q A G Q K A E N L T P D E V S K R E G I N A E Q   PhtD.PRO
  1     C S Y E L G R Y Q A G Q D K K E S N R V A Y I D G D Q A G Q K A E N L T P D E V S K R E G I N A E Q   PhtB.pro
  1     C S Y E L G L Y Q A - R T V K E N N R V S Y I D G K Q A T Q K T E N L T P D E V S K R E G I N A E Q   PhtA.PRO
  1     C A Y A L N Q H R S - Q E N K D N R V S Y V D G S Q S S Q K S E N L T P D Q V S Q K E G I Q A E Q     PhtE.PRO I V I K I T D Q G Y V T S H G D H Y H Y Y N G K V P Y D A I I S E E L L M K D P N Y Q L K D S D I V  Majority
                    60                  70                  80                  90                  100
 51     I V I K I T D Q G Y V T S H G D H Y H Y Y N G K V P Y D A I I S E E L L M K D P N Y Q L K D S D I V   PhtD.PRO
 51     I V I K I T D Q G Y V T S H G D H Y H Y Y N G K V P Y D A I I S E E L L M K D P N Y Q L K D S D I V   PhtB.pro
 50     I V I K I T D Q G Y V T S H G D H Y H Y Y N G K V P Y D A I I S E E L L M K D P N Y K L K D E D I V   PhtA.PRO
 50     I V I K I T D Q G Y V T S H G D H Y H Y Y N G K V P Y D A L F S E E L L M K D P N Y Q L K D A D I V   PhtE.PRO N E V K G G Y V I K V D G K Y Y V Y L K D A A H A D N V R T K E E I N R Q K Q E H S H N H E G G - - Majority
                    110                 120                 130                 140                 150
101     N E I K G G Y V I K V D G K Y Y V Y L K D A A H A D N I R T K E E I K R Q K Q E H S H N H G G - -     PhtD.PRO
101     N E I K G G Y V I K V N G K Y Y V Y L K D A A H A D N I R T K E E I K R Q K Q E R S H N H N S - - -   PhtB.pro
100     N E V K G G Y V I K V D G K Y Y V Y L K D A A H A D N V R T K E E I N R Q K Q E H S Q H R E G G T P   PhtA.PRO
100     N E V K G G Y I I K V D G K Y Y V Y L K D A A H A D N V R T K D E I N R Q K Q E H V K D N E - - -     PhtE.PRO R N D X A V A A A R A Q G R Y T T D D G Y I P N A S D I I E D T G D A Y I V P H G D H Y H Y I P K N Majority
                    160                 170                 180                 190                 200
149     S N D Q A V V A A R A Q G R Y T T D D G Y I P N A S D I I E D T G D A Y I V P H G D H Y H Y I P K N   PhtD.PRO
148     R A D N A V A A A R A Q G R Y T T D D G Y I P N A S D I I E D T G D A Y I V P H G D H Y H Y I P K N   PhtB.pro
150     R N D G A V A L A R S Q G R Y T T D D G Y I P N A S D I I E D T G D A Y I V P H G D H Y H Y I P K N   PhtA.PRO
146     K V N S N V A V A R S Q G R Y T T N D G Y V P N P A D I I E D T G N A Y I V P H G H Y H Y I P K S     PhtE.PRO E L S A S E L A A A E A Y L N G K - - - - - - - - - - - - Q G S R P S S S S Y N A N P A Q P R L S E Majority
                    210                 220                 230                 240                 250
199     E L S A S E L A A A E A Y W N G K - - - - - - - - - - - - Q G S R P S S S S Y N A N P A Q P R L S E   PhtD.PRO
198     E L S A S E L A A A E A Y W N G K - - - - - - - - - - - - Q G S R P S S S S Y N A N P A Q P R L S E   PhtB.pro
200     E L S A S E L A A A E A F L S G R G N L S N S R T Y R R Q N S D N T S R T N W V P S V S N P G T T N   PhtA.PRO
196     D L S A S E L A A A K A H L A G K - - - - - - - - - - - - - N M Q P S Q L S Y S S T A S D - - - N N   PhtE.PRO T H N L T V T P T Y H Q A N Q G E N I S S L L K E L Y A K P L S E R H V E S D G L V F D P A Q I T S Majority
                    260                 270                 280                 290                 300
238     N H N L T V T P T Y H Q - N Q G E N I S S L L R E L Y A K P L S E R H V E S D G L I F D P A Q I T S   PhtD.PRO
237     N H N L T V T P T Y H Q - N Q G E N I S S L L R E L Y A K P L S E R H V E S D G L I F D P A Q I T S   PhtB.pro
250     T N T S N N S N T N S Q A S Q S N D I D S L L K Q L Y K L P L S Q R H V E S D G L V F D P A Q I T S   PhtA.PRO
230     T Q S V A K G S T S K P A N K S E N L Q S L L K E L Y D S P S A Q R Y S E D G L V F D P A K I I S     PhtE.PRO R T A R G V A V P H G D H Y H F I P Y S Q M S E L E E R I A R I I P L R Y S N H W V P D S R P E Q   Majority
                    310                 320                 330                 340                 350
287     R T A R G V A V P H G N H Y H F I P Y E Q M S E L E K R I A R I I P L R Y S N H W V P D S R P E Q     PhtD.PRO
286     R T A R G V A V P H G N H Y H F I P Y E Q M S E L E K R I A R I I P L R Y S N H W V P D S R P E E     PhtB.pro
300     R T A R G V A V P H G D H Y H F I P Y S Q M S E L E E R I A R I I P L R Y S N H W V P D S R P E Q     PhtA.PRO
280     R T P N G V A I P H G D H Y H F I P Y S L S A L E E K I A R M V P I - - - - - - - - - - - - - -     PhtE.PRO
```

Figure 6(b)

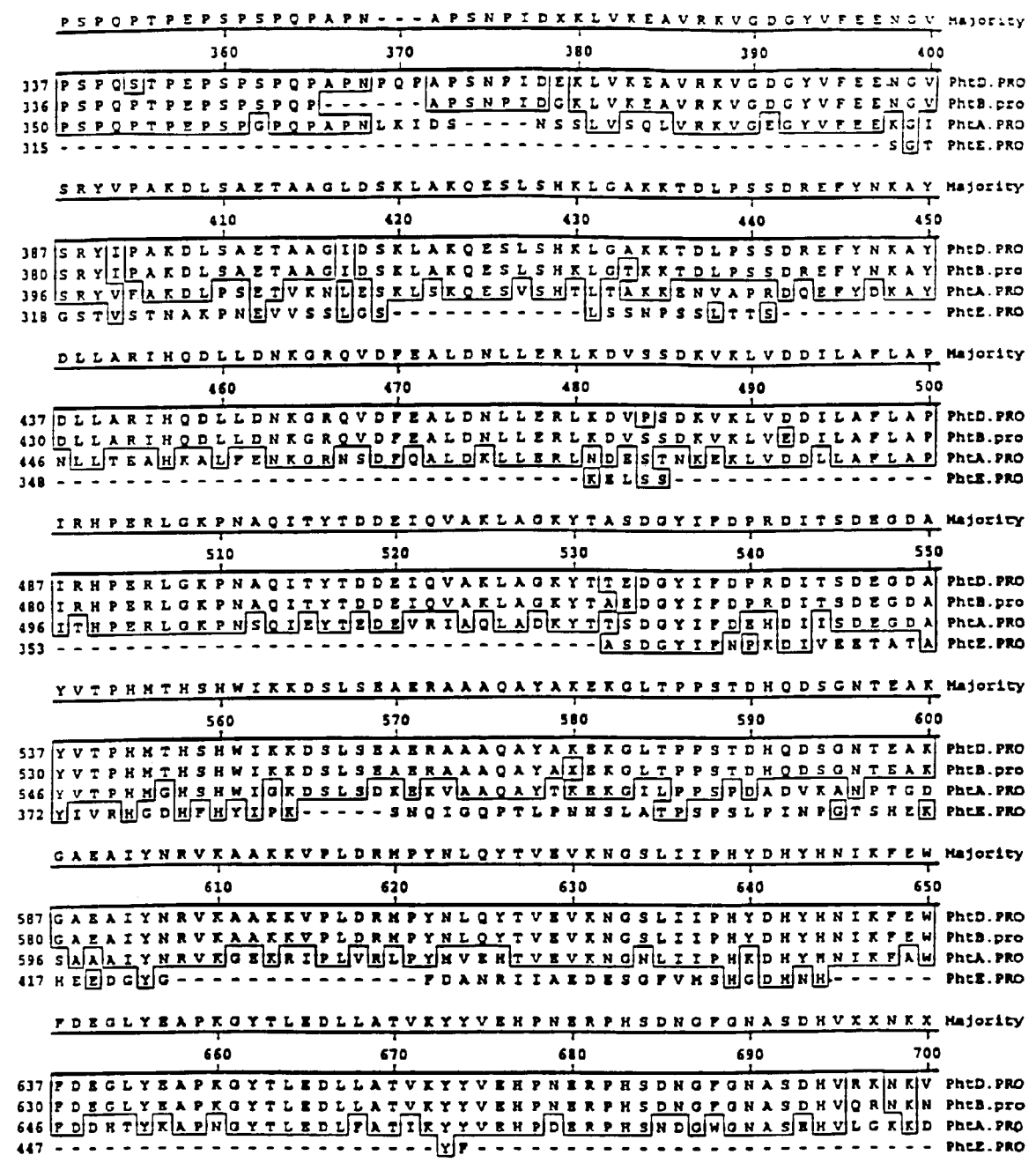

[Sequence alignment figure showing protein sequences PhtD.PRO, PhtB.pro, PhtA.PRO, and PhtE.PRO aligned against a Majority consensus sequence, spanning residues approximately 350-700.]

Figure 6(c)

```
     X Q X D X N X X X K X X E E X      - - - P E - - - - - - - - - - - P - - - - - - - - - - - - - - - - - - - Majority
                     710              720           730           740           750
687  D Q D S K P D E D K E H D E V S E P T H P E S D E K E N H A G L N P S A D N L Y K P S T D T E E T E   PhtD.PRO
680  G Q A D T N Q T E K P S E E K P Q T E K P E E E T - - - - - - - P R E E K P Q S E K P E S P K P T     PhtB.pro
696  H S E D P N K N F K A D E E P - - - - - - - - - - - - - - - - - - - - - - - - - - - - - - - - -     PhtA.PRO
449  - - - - - - - - - - - - - - - - - - - - - - - - - - - - - - - - - - - - - - - - - - - - - - - -     PhtE.PRO E E X E E T P X E X E X P Q V E T E K V E A K L X E A E X L L X K V T D P S I K X N A X E T L T G L   Majority
                     760              770           780           790           800
737  E E A E D T T D E A E I P Q V E N S V I N A X I A D A E A L L E K V T D P S I R Q N A M E T L T G L   PhtD.PRO
722  E E P E S P E E S E E P Q V E T E K V E E K L R E A E D L L G K I Q D P I I K S N A K E T L T G L     PhtB.pro
711  - - V E E T P A E P E V P Q V E T E K V E A Q L K E A E V L L A K V T D S S L K A N A T E T L A G L   PhtA.PRO
449  - - - - - - - - - - - - - - - F K K D L T E E Q I - - - - - - - - - - - - - - - - - - - - - - -     PhtE.PRO K N N L L L G T X D N N T I M A E A E K L L A L L K E S X P X X X - - - K - - K - -                   Majority
                     810              820           830           840
787  K S S L L L G T K D N N T I S A E V D S L L A L L K E S Q P A P I                                     PhtD.PRO
772  K N N L L F G T Q D N N T I M A E A E K L L A L L K E S K                                             PhtB.pro
759  R N N L T L Q I K D N N S I M A E A E K L L A L L K G S N P S S V S K E K I N K L N                   PhtA.PRO
459  - - - - - - - - - - - - - - - - - - - - - - - - - - - - - - K V R K N I                             PhtE.PRO
```

Decoration 'Decoration #2': Box residues that match the Consensus exactly.

Figure 7(a)

```
    TCCTATGAGCTTGGA_ GTTATCAAGCTGGTCAGGTTAAGAAAGAGTCTAA  Majority
              10         20         30         40         50
 61 TCTTACGAGTTGGGACTGTATCAAGCTAGAACGGTTAAGGAAAA---TAA  phtA.SEQ
  1 TCCTATGAGCTTGGACGTTACCAAGCTGGTCAGGATAAGAAAGAGTCTAA  phtB.seq
  1 TCCTATGAACTTGGTCGTCACCAAGCTGGTCAGGTTAAGAAAGAGTCTAA  phtD.SEQ
 64 GCCTATGCACTAAACCAGCATC--GTTCG-CAGGAAAATAAGGACAATAA  phtE.SEQ TCGTGTTTCTTATATAGATGGTGATCAGGCTGGTCAAAAGGCAGAAAACT  Majority
              60         70         80         90        100
108 TCGTGTTTCCTATATAGATGGAAAACAAGCGACGCAAAAAACGGAGAATT  phtA.SEQ
 51 TCGAGTTGCTTATATAGATGGTGATCAGGCTGGTCAAAAGGCAGAAAACT  phtB.seq
 51 TCGAGTTTCTTATATAGATGGTGATCAGGCTGGTCAAAAGGCAGAAAACT  phtD.SEQ
111 TCGTGTCTCTTATGTGGATGGCAGCCAGTCAAGTCAGAAAAGTGAAAACT  phtE.SEQ TGACACCAGATGAGGTTAGTAAGAGGGAGGGGATCAACGCTGAGCAAATT  Majority
             110        120        130        140        150
158 TGACTCCTGATGAGGTTAGCAAGCGTGAAGGAATCAATGCTGAGCAAATC  phtA.SEQ
101 TGACACCAGATGAAGTCAGTAAGAGGGAGGGGATCAACGCCGAACAAATT  phtB.seq
101 TGACACCAGATGAAGTCAGTAAGAGGGAGGGGATCAACGCCGAACAAATC  phtD.SEQ
161 TGACACCAGACCAGGTTAGCCAGAAAGAAGGAATTCAGGCTGAGCAAATT  phtE.SEQ GTCATCAAGATTACGGATCAAGGTTATGTGACCTCTCATGGAGACCATTA  Majority
             160        170        180        190        200
208 GTCATCAAGATAACAGACCAAGGCTATGTCACTTCACATGGCGACCACTA  phtA.SEQ
151 GTTATCAAGATTACGGATCAAGGTTATGTGACCTCTCATGGAGACCATTA  phtB.seq
151 GTCATCAAGATTACGGATCAAGGTTATGTGACCTCTCATGGAGACCATTA  phtD.SEQ
211 GTAATCAAAATTACAGATCAGGGCTATGTAACGTCACACGGTGACCACTA  phtE.SEQ TCATTACTATAATGGCAAGGTTCCTTATGATGCCATCATCAGTGAAGAGC  Majority
             210        220        230        240        250
258 TCATTATTACAATGGTAAGGTTCCTTATGACGCTATCATCAGTGAAGAAT  phtA.SEQ
201 TCATTACTATAATGGCAAGGTTCCTTATGATGCCATCATCAGTGAAGAGC  phtB.seq
201 TCATTACTATAATGGCAAGGTCCCTTATGATGCCATCATCAGTGAAGAGC  phtD.SEQ
261 TCATTACTATAATGGGAAAGTTCCTTATGATGCCCTCTTTAGTGAAGAAC  phtE.SEQ TCCTCATGAAAGATCCGAATTATCAGTTGAAGGATTCAGATATTGTCAAT  Majority
             260        270        280        290        300
308 TACTCATGAAAGATCCAAAACTATAAGCTAAAAGATGAGGATATTGTTAAT  phtA.SEQ
251 TCCTCATGAAAGATCCGAATTATCAGTTGAAGGATTCAGACATTGTCAAT  phtB.seq
251 TCCTCATGAAAGATCCGAATTATCAGTTGAAGGATTCAGACATTGTCAAT  phtD.SEQ
311 TCTTGATGAAGGATCCAAACTATCAACTTAAAGACGCTGATATTGTCAAT  phtE.SEQ GAAGTCAAGGGTGGTTATGTTATCAAGGTAGATGGAAAATACTATGTTTA  Majority
             310        320        330        340        350
358 GAGGTCAAGGGTGGATATGTTATCAAGGTAGATGGAAAATACTATGTTTA  phtA.SEQ
301 GAAATCAAGGGTGGTTATGTCATTAAGGTAAACGGTAAATACTATGTTTA  phtB.seq
301 GAAATCAAGGGTGGTTATGTTATCAAGGTAGATGGAAAATACTATGTTTA  phtD.SEQ
361 GAAGTCAAGGGTGGTTATATCATCAAGGTCGATGGAAAATATTATGTCTA  phtE.SEQ
```

Figure 7(b)

```
          C C T T A A G G A T G C A G C   C A T G C G G A T A A T G T T C G G A C A A A A G A A G A G A T T A   Majority
                    360               370               380               390               400
      408 C C T T A A G G A T G C T G C C C A C G C G G A T A A C G T C C G T A C A A A A G A G G A A A T C A   phtA.SEQ
      351 C C T T A A G G A T G C R G C T C A T G C G G A T A A T A T T C G G A C A A A A G A A G A G A T T A   phtB.seq
      351 C C T T A A G G A T G C A G C T C A T G C G G A T A A T A T T C G G A C A A A A G A A G A G A T T A   phtD.SEQ
      411 C C T G A A A G A T G C A G C T C A T G C T G A T A A T G T T C G A A C T A A A G A T G A A A T C A   phtE.SEQ A T C G T C A G A A G C A G G A A C A T A G T C A T A A T C A T G A G G G T G G A X C T - - - A - -   Majority
                    410               420               430               440               450
      458 A T C G A C A A A A A C A A G A G C A T A G T C A A C A T C G T G A A G G T G G A A C T C C A A G A   phtA.SEQ
      401 A A C G T C A G A A G C A G G A A C G C A G T C A T A A T C A T A A C T C A A G A G C A - - - - - -   phtB.seq
      401 A A C G T C A G A A G C A G G A A C A C A G T C A T A A T C A C G G G G T G G T T C T - - - - - -     phtD.SEQ
      461 A T C G T C A A A A A C A A G A A C A T G T C A A A G A T A A T G A G - - - - - - - - - - - A A G     phtE.SEQ G A T G A T X X T G C T G T T G C T G T A G C C A G A T C C C A A G G A C G C T A T A C A A C G G A   Majority
                    460               470               480               490               500
      508 A A C G A T G G T G C T G T T G C C T T G G C A C G T T C G C A A G G A C G C T A T A C T A C A G A   phtA.SEQ
      445 G A T A A T - - - G C T G T T G C T G C A G C C A G A G C C C A A G G A C G T T A T A C A A C G G A   phtB.seq
      445 A A C G A T C A A G C A G T A G T T G C A G C C A G A G C C C A A G G A C G C T A T A C A A C G G A   phtD.SEQ
      499 G T T A A C T C T A A T G T T G C T G T A G C A A G G T C T C A G G G A C G A T A T A C G A C A A A   phtE.SEQ T G A T G G T T A T A T C T T T A A T G C A T C T G A T A T C A T T G A G G A T A C G G G T G A T G   Majority
                    510               520               530               540               550
      558 T G A T G G T T A T A T C T T T A A T G C T T C T G A T A T C A T A G A G G A T A C T G G T G A T G   phtA.SEQ
      492 T G A T G G G T A T A T C T T C A A T G C A T C T G A T A T C A T T G A G G A C A C G G G T G A T G   phtB.seq
      495 T G A T G G T T A T A T C T T C A A T G C A T C T G A T A T C A T T G A G G A C A C G G G T G A T G   phtD.SEQ
      549 T G A T G G T T A T G T C T T T A A T C C A G C T G A T A T T A T C G A A G A T A C G G G T A A T G   phtE.SEQ C T T A T A T C G T T C C T C A T G G C G A T C A T T A C C A T T A C A T T C C T A A G A A T G A G   Majority
                    560               570               580               590               600
      608 C T T A T A T C G T T C C T C A T G G A G A T C A T T A C C A T T A C A T T C C T A A G A A T G A G   phtA.SEQ
      542 C T T A T A T C G T T C C T C A C G G C G A C C A T T A C C A T T A C A T T C C T A A G A A T G A G   phtB.seq
      545 C T T A T A T C G T T C C T C A C G G C G A C C A T T A C C A T T A C A T T C C T A A G A A T G A G   phtD.SEQ
      599 C T T A T A T C G T T C C T C A T G G A G G T C A C T A T C A C T A C A T T C C C A A A A G C G A T   phtE.SEQ T T A T C A G C T A G C G A G T T A G C T G C T G C A G A A G C C - - - - T A T T T G G A T G G G A   Majority
                    610               620               630               640               650
      658 T T A T C A G C T A G C G A G T T G G C T G C T G C A G A A G C C T T C C T A T C T G G T C G A G G   phtA.SEQ
      592 T T A T C A G C T A G C G A G T T A G C T G C T G C A G A A G C C - - - - T A T T G G A A T G G G A   phtB.seq
      595 T T A T C A G C T A G C G A G T T A G C T G C T G C A G A A G C C - - - - T A T T G G A A T G G G A   phtD.SEQ
      649 T T A T C T G C T A G T G A A T T A G C A G C A G C T A A A G C A C - - - - A T C T G G C T G G A A   phtE.SEQ A G - - - - - - C A A A T - - G G G A T C T C G T C C T T C T T C A A G T T C T A G T T A T A C T T   Majority
                    660               670               680               690               700
      708 A A A T C T G T C A A A T T C A A G A A C C T A T C G C C G A C A A A A T A G C G A T A A C A C T T   phtA.SEQ
      638 A G - - - - - - C A - - - - - G G G A T C T C G T C C T T C T T C A A G T T C T A G T T A T A A T G   phtB.seq
      641 A G - - - - - - C A - - - - - G G G A T C T C G T C C T T C T T C A A G T T C T A G T T A T A A T G   phtD.SEQ
      695 A - - - - - - - - A A A T A T G C A A C C G A G T C - - - - - - - - A G T T A - A G C T A T T C T T   phtE.SEQ
```

Figure 7D:
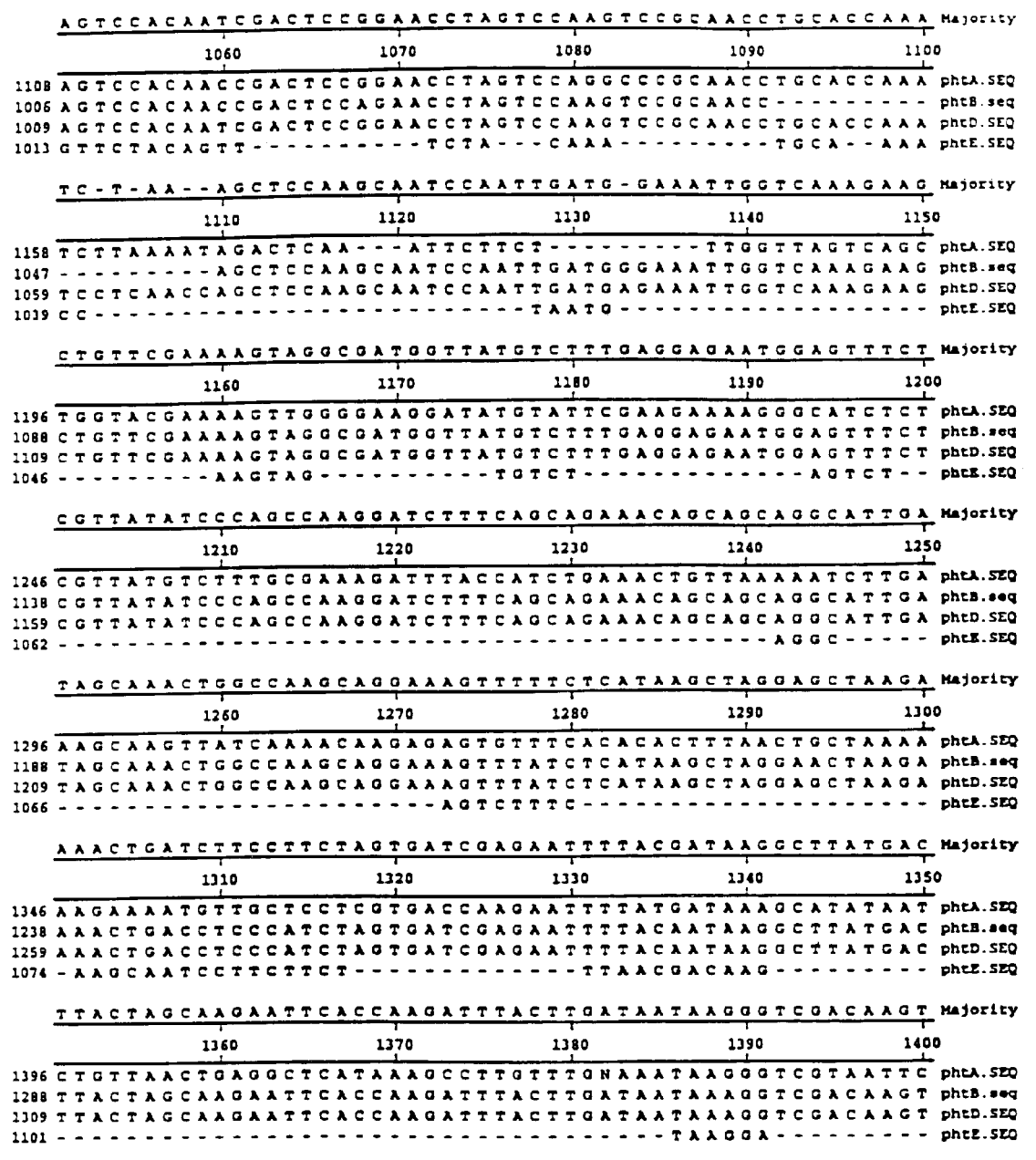

[Figure: DNA sequence alignment showing Majority consensus with phtA.SEQ, phtB.seq, phtD.SEQ, and phtE.SEQ sequences across positions 1060–1400]

```
     C A G A A A G A C T A T T G G C T T T G T T A A A G G A G A G T A A X T - A A G G T - - - - - C T T   Majority
                    |                   |                   |                   |                   |
                  2460                2470                2480                2490                2500

2384 C A G A A A A A T T A C T T G C G T T G T T A A A A G G A A G T A A T C - - - - - - - - - - - C T T   phtA.SEQ
2363 C T G A A A A A C T A T T G G C T T T A T T A A A G G A G A G T A A G T A A A G G T A G A A G C T T   phtB.seq
2408 T A G A T A G T C T C T T G G C T T T G T T A A A A G A A A G T - - - - - - - - - - - - - - - - - C   phtD.SEQ
1409 - A G A A G G A C T - - T G A C - - - - - - - - A G A A G A G C A A A T T A A G G T - - - - - - - -   phtE.SEQ A A - - G C G - - T C T G G C - C C T A - G - C A A - A A - A - T - - T A T G G X A A A A G C T X A   Majority
                    |                   |                   |                   |                   |
                  2510                2520                2530                2540                2550

2423 C A - - - - - - - T C T G - - - - - T A A G - - - - - - - - - - - - T A A G G A A A A A A T - - -   phtA.SEQ
2413 A A G G G C G A A T T T G G C A C C C A G G A C A A C A A T A C T A T T A T G G C A G A A G C T G A   phtB.seq
2441 A A - - - - - - - - C C G G C T C C T A - - - - - - - - - - - - - - - T A T A G T A A A A G C T T A   phtD.SEQ
1440 - - - - G C G - - - - - - - - - - - - - - - - C A A A A A C A T T - - - - T A G                       phtE.SEQ A A A A C T A X X                                                                                     Majority 2445 - A A A C T A A                                                                                       phtA.SEQ
2463 A A A A C T A T T                                                                                     phtB.seq
2468 A G - - - - - C C                                                                                     phtD.SEQ
1455                                                                                                       phtE.SEQ
```

A. Strain SJ2 (serotype 6B)

B. Strain EF6796 (serotype 6A)

C. Strain EF5668 (serotype 4)

SEQUENCE LISTING

<160> NUMBER OF SEQ ID NOS: 14

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Forward
      primer used in amplification of the Sp36 gene sequence.

<400> SEQUENCE: 1
atcggatcct tcttacgagt tgggactgta tcaagc                                  36

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Forward
      primer used in amplification of the Sp36 gene sequence.

<400> SEQUENCE: 2
atcggatcca ctgtatcaag ctagaacggt taagg                                   35

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Reverse
      primer used in amplification of the Sp36 gene sequence.

<400> SEQUENCE: 3
agtcaagctt gtttattttt tccttactta cagatgaagg                              40

<210> SEQ ID NO 4
<211> LENGTH: 838
<212> TYPE: PRT
<213> ORGANISM: Streptococcus pneumoniae

<400> SEQUENCE: 4

Met Lys Ile Asn Lys Lys Tyr Leu Ala Gly Ser Val Ala Val Leu Ala
 1               5                  10                  15

Leu Ser Val Cys Ser Tyr Glu Leu Gly Arg His Gln Ala Gly Gln Val
                20                  25                  30

Lys Lys Glu Ser Asn Arg Val Ser Tyr Ile Asp Gly Asp Gln Ala Gly
            35                  40                  45

Gln Lys Ala Glu Asn Leu Thr Pro Asp Glu Val Ser Lys Arg Glu Gly
        50                  55                  60

Ile Asn Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Ile Ile Ser Glu Glu Leu Leu Met Lys Asp Pro Asn Tyr Gln
                100                 105                 110

Leu Lys Asp Ser Asp Ile Val Asn Glu Ile Lys Gly Gly Tyr Val Ile
            115                 120                 125

Lys Val Asp Gly Lys Tyr Tyr Val Tyr Leu Lys Asp Ala Ala His Ala
        130                 135                 140

Asp Asn Ile Arg Thr Lys Glu Glu Ile Lys Arg Gln Lys Gln Glu His

-continued

```
            145                 150                 155                 160
Ser His Asn His Gly Gly Ser Asn Asp Gln Ala Val Ala Ala
                165                 170                 175
Arg Ala Gln Gly Arg Tyr Thr Thr Asp Asp Gly Tyr Ile Phe Asn Ala
                180                 185                 190
Ser Asp Ile Ile Glu Asp Thr Gly Asp Ala Tyr Ile Val Pro His Gly
                195                 200                 205
Asp His Tyr His Tyr Ile Pro Lys Asn Glu Leu Ser Ala Ser Glu Leu
            210                 215                 220
Ala Ala Ala Glu Ala Tyr Trp Asn Gly Lys Gln Gly Ser Arg Pro Ser
225                 230                 235                 240
Ser Ser Ser Tyr Asn Ala Asn Pro Ala Gln Pro Arg Leu Ser Glu
                245                 250                 255
Asn His Asn Leu Thr Val Thr Pro Thr Tyr His Gln Asn Gln Gly Glu
                260                 265                 270
Asn Ile Ser Ser Leu Leu Arg Glu Leu Tyr Ala Lys Pro Leu Ser Glu
                275                 280                 285
Arg His Val Glu Ser Asp Gly Leu Ile Phe Asp Pro Ala Gln Ile Thr
            290                 295                 300
Ser Arg Thr Ala Arg Gly Val Ala Val Pro His Gly Asn His Tyr His
305                 310                 315                 320
Phe Ile Pro Tyr Glu Gln Met Ser Glu Leu Glu Lys Arg Ile Ala Arg
                325                 330                 335
Ile Ile Pro Leu Arg Tyr Arg Ser Asn His Trp Val Pro Asp Ser Arg
                340                 345                 350
Pro Glu Gln Pro Ser Pro Gln Ser Thr Pro Glu Pro Ser Pro Ser Pro
            355                 360                 365
Gln Pro Ala Pro Asn Pro Gln Pro Ala Pro Ser Asn Pro Ile Asp Glu
            370                 375                 380
Lys Leu Val Lys Glu Ala Val Arg Lys Val Gly Asp Gly Tyr Val Phe
385                 390                 395                 400
Glu Glu Asn Gly Val Ser Arg Tyr Ile Pro Ala Lys Asp Leu Ser Ala
                405                 410                 415
Glu Thr Ala Ala Gly Ile Asp Ser Lys Leu Ala Lys Gln Glu Ser Leu
                420                 425                 430
Ser His Lys Leu Gly Ala Lys Lys Thr Asp Leu Pro Ser Ser Asp Arg
            435                 440                 445
Glu Phe Tyr Asn Lys Ala Tyr Asp Leu Leu Ala Arg Ile His Gln Asp
            450                 455                 460
Leu Leu Asp Asn Lys Gly Arg Gln Val Asp Phe Glu Ala Leu Asp Asn
465                 470                 475                 480
Leu Leu Glu Arg Leu Lys Asp Val Pro Ser Asp Lys Val Lys Leu Val
                485                 490                 495
Asp Asp Ile Leu Ala Phe Leu Ala Pro Ile Arg His Pro Glu Arg Leu
                500                 505                 510
Gly Lys Pro Asn Ala Gln Ile Thr Tyr Thr Asp Asp Glu Ile Gln Val
                515                 520                 525
Ala Lys Leu Ala Gly Lys Tyr Thr Thr Glu Asp Gly Tyr Ile Phe Asp
                530                 535                 540
Pro Arg Asp Ile Thr Ser Asp Glu Gly Asp Ala Tyr Val Thr Pro His
545                 550                 555                 560
Met Thr His Ser His Trp Ile Lys Lys Asp Ser Leu Ser Glu Ala Glu
                565                 570                 575
```

```
Arg Ala Ala Ala Gln Ala Tyr Ala Lys Glu Lys Gly Leu Thr Pro Pro
            580                 585                 590

Ser Thr Asp His Gln Asp Ser Gly Asn Thr Glu Ala Lys Gly Ala Glu
        595                 600                 605

Ala Ile Tyr Asn Arg Val Lys Ala Ala Lys Lys Val Pro Leu Asp Arg
    610                 615                 620

Met Pro Tyr Asn Leu Gln Tyr Thr Val Glu Val Lys Asn Gly Ser Leu
625                 630                 635                 640

Ile Ile Pro His Tyr Asp His Tyr His Asn Ile Lys Phe Glu Trp Phe
                645                 650                 655

Asp Glu Gly Leu Tyr Glu Ala Pro Lys Gly Tyr Thr Leu Glu Asp Leu
            660                 665                 670

Leu Ala Thr Val Lys Tyr Tyr Val Glu His Pro Asn Glu Arg Pro His
        675                 680                 685

Ser Asp Asn Gly Phe Gly Asn Ala Ser Asp His Val Arg Lys Asn Lys
    690                 695                 700

Val Asp Gln Asp Ser Lys Pro Asp Glu Asp Lys Glu His Asp Glu Val
705                 710                 715                 720

Ser Glu Pro Thr His Pro Glu Ser Asp Glu Lys Glu Asn His Ala Gly
                725                 730                 735

Leu Asn Pro Ser Ala Asp Asn Leu Tyr Lys Pro Ser Thr Asp Thr Glu
            740                 745                 750

Glu Thr Glu Glu Glu Ala Glu Asp Thr Thr Asp Glu Ala Glu Ile Pro
        755                 760                 765

Gln Val Glu Asn Ser Val Ile Asn Ala Lys Ile Ala Asp Ala Glu Ala
    770                 775                 780

Leu Leu Glu Lys Val Thr Asp Pro Ser Ile Arg Gln Asn Ala Met Glu
785                 790                 795                 800

Thr Leu Thr Gly Leu Lys Ser Ser Leu Leu Gly Thr Lys Asp Asn
                805                 810                 815

Asn Thr Ile Ser Ala Glu Val Asp Ser Leu Leu Ala Leu Leu Lys Glu
            820                 825                 830

Ser Gln Pro Ala Pro Ile
        835

<210> SEQ ID NO 5
<211> LENGTH: 2531
<212> TYPE: DNA
<213> ORGANISM: Streptococcus pneumoniae

<400> SEQUENCE: 5
atgaaaatta taaaaaata  tctagcaggt  tcagtggcag  tccttgccct  aagtgtttgt    60
tcctatgaac ttggtcgtca  ccaagctggt  caggttaaga  aagagtctaa  tcgagtttct   120
tatatagatg gtgatcaggc  tggtcaaaag  gcagaaaact  tgacaccaga  tgaagtcagt   180
aagagggagg ggatcaacgc  cgaacaaatc  gtcatcaaga  ttacggatca  aggttatgtg   240
acctctcatg gagaccatta  tcattactat  aatggcaagg  tcccttatga  tgccatcatc   300
agtgaagagc tcctcatgaa  agatccgaat  tatcagttga  aggattcaga  cattgtcaat   360
gaaatcaagg gtggttatgt  tatcaaggta  gatggaaaat  actatgttta  ccttaaggat   420
gcagctcatg cggataatat  tcggacaaaa  gaagagatta  acgtcagaa  gcaggaacac   480 agtcataatc acgggggtgg  ttctaacgat  caagcagtag  ttgcagccag  agcccaagga   540
cgctatacaa cggatgatgg  ttatatcttc  aatgcatctg  atatcattga  ggacacgggt   600
```

```
gatgcttata tcgttcctca cggcgaccat taccattaca ttcctaagaa tgagttatca    660
gctagcgagt tagctgctgc agaagcctat tggaatggga agcagggatc tcgtccttct    720
tcaagttcta gttataatgc aaatccagct caaccaagat tgtcagagaa ccacaatctg    780
actgtcactc aacttatca tcaaaatcaa ggggaaaaca tttcaagcct tttacgtgaa    840
ttgtatgcta aaccttatc agaacgccat gtggaatctg atggccttat tttcgaccca    900
gcgcaaatca caagtcgaac cgccagaggt gtagctgtcc ctcatggtaa ccattaccac    960
tttatccctt atgaacaaat gtctgaattg gaaaaacgaa ttgctcgtat tattcccctt   1020
cgttatcgtt caaaccattg ggtaccagat tcaagaccag aacaaccaag tccacaatcg   1080
actccggaac ctagtccaag tccgcaacct gcaccaaatc ctcaaccagc tccaagcaat   1140
ccaattgatg agaaattggt caagaagct gttcgaaaag taggcgatgg ttatgtcttt   1200
gaggagaatg gagtttctcg ttatatccca gccaaggatc tttcagcaga acagcagca   1260 ggcattgata gcaaactggc caagcaggaa agtttatctc ataagctagg agctaagaaa   1320
actgacctcc catctagtga tcgagaattt tacaataagg cttatgactt actagcaaga   1380
attcaccaag atttacttga taataaaggt cgacaagttg attttgaggc tttggataac   1440
ctgttggaac gactcaagga tgtcccaagt gataaagtca gttagtgga tgatattctt   1500 gccttcttag ctccgattcg tcatccgaaa cgtttaggaa accaaatgc gcaaattacc   1560 tacactgatg atgagattca gtagccaag ttggcaggca gtacacaac agaagacggt   1620 tatatctttg atcctcgtga tataaccagt gatgaggggg atgcctatgt aactccacat   1680
atgacccata gccactggat taaaaagat agtttgtctg aagctgagag agcggcagcc   1740
caggcttatg ctaaagagaa aggtttgacc cctccttcga cagaccatca ggattcagga   1800
aatactgagg caaaggagc agaagctatc tacaaccgcg tgaaagcagc taagaaggtg   1860
ccacttgatc gtatgcctta caatcttcaa tatactgtag aagtcaaaaa cggtagttta   1920
atcatacctc attatgacca ttaccataac atcaaatttg agtggtttga cgaaggcctt   1980
tatgaggcac ctaaggggta tactcttgag gatcttttgg cgactgtcaa gtactatgtc   2040
gaacatccaa acgaacgtcc gcattcagat aatggttttg gtaacgctag cgaccatgtt   2100
cgtaaaaata aggtagacca agacagtaaa cctgatgaag ataaggaaca tgatgaagta   2160
agtgagccaa ctcaccctga atctgatgaa aaagagaatc acgctggttt aaatccttca   2220
gcagataatc tttataaacc aagcactgat acggaagaga cagaggaaga agctgaagat   2280
accacagatg aggctgaaat tcctcaagta gagaattctg ttattaacgc taagatagca   2340
gatgcggagg ccttgctaga aaagtaaca gatcctagta ttagacaaaa tgctatggag   2400
acattgactg gtctaaaaag tagtcttctt ctcggaacga agataataa cactatttca   2460 gcagaagtag atagtctctt ggctttgtta aagaaagtc aaccggctcc tatatagtaa   2520
aagcttaagc c                                                       2531
```

<210> SEQ ID NO 6
<211> LENGTH: 484
<212> TYPE: PRT
<213> ORGANISM: Streptococcus pneumoniae

<400> SEQUENCE: 6

```
Met Lys Phe Ser Lys Lys Tyr Ile Ala Ala Gly Ser Ala Val Ile Val
 1               5                  10                  15

Ser Leu Ser Leu Cys Ala Tyr Ala Leu Asn Gln His Arg Ser Gln Glu
```

-continued

```
                    20                  25                  30
Asn Lys Asp Asn Asn Arg Val Ser Tyr Val Asp Gly Ser Gln Ser Ser
            35                  40                  45

Gln Lys Ser Glu Asn Leu Thr Pro Asp Gln Val Ser Gln Lys Glu Gly
        50                  55                  60

Ile Gln Ala Glu Gln Ile Val Ile Lys Ile Thr Asp Gln Gly Tyr Val
65                  70                  75                  80

Thr Ser His Gly Asp His Tyr His Tyr Asn Gly Lys Val Pro Tyr
                85                  90                  95

Asp Ala Leu Phe Ser Glu Glu Leu Leu Met Lys Asp Pro Asn Tyr Gln
                100                 105                 110

Leu Lys Asp Ala Asp Ile Val Asn Glu Val Lys Gly Gly Tyr Ile Ile
            115                 120                 125

Lys Val Asp Gly Lys Tyr Tyr Val Tyr Leu Lys Asp Ala His Ala
            130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
                180                 185                 190

Ile Ile Glu Asp Thr Gly Asn Ala Tyr Ile Val Pro His Gly Gly His
            195                 200                 205

Tyr His Tyr Ile Pro Lys Ser Asp Leu Ser Ala Ser Glu Leu Ala Ala
210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu
                260                 265                 270

Lys Glu Leu Tyr Asp Ser Pro Ser Ala Gln Arg Tyr Ser Glu Ser Asp
            275                 280                 285

Gly Leu Val Phe Asp Pro Ala Lys Ile Ile Ser Arg Thr Pro Asn Gly
            290                 295                 300

Val Ala Ile Pro His Gly Asp His Tyr His Phe Ile Pro Tyr Ser Lys
305                 310                 315                 320

Leu Ser Ala Leu Glu Glu Lys Ile Ala Arg Met Val Pro Ile Ser Gly
                325                 330                 335

Thr Gly Ser Thr Val Ser Thr Asn Ala Lys Pro Asn Glu Val Val Ser
                340                 345                 350

Ser Leu Gly Ser Leu Ser Ser Asn Pro Ser Ser Leu Thr Thr Ser Lys
            355                 360                 365

Glu Leu Ser Ser Ala Ser Asp Gly Tyr Ile Phe Asn Pro Lys Asp Ile
            370                 375                 380

Val Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
                405                 410                 415

Asn Ser Leu Ala Thr Pro Ser Pro Ser Leu Pro Ile Asn Pro Gly Thr
            420                 425                 430

Ser His Glu Lys His Glu Glu Asp Gly Tyr Gly Phe Asp Ala Asn Arg
            435                 440                 445
```

```
Ile Ile Ala Glu Asp Glu Ser Gly Phe Val Met Ser His Gly Asp His
    450                 455                 460

Asn His Tyr Phe Phe Lys Lys Asp Leu Thr Glu Glu Gln Ile Lys Val
465                 470                 475                 480

Arg Lys Asn Ile

<210> SEQ ID NO 7
<211> LENGTH: 1455
<212> TYPE: DNA
<213> ORGANISM: Streptococcus pneumoniae

<400> SEQUENCE: 7
atgaaattta gtaaaaaata tatagcagct ggatcagctg ttatcgtatc cttgagtcta     60
tgtgcctatg cactaaacca gcatcgttcg caggaaaata aggacaataa tcgtgtctct    120
tatgtggatg gcagccagtc aagtcagaaa agtgaaaact tgacaccaga ccaggttagc    180 cagaagaag gaattcaggc tgagcaaatt gtaatcaaaa ttacagatca gggctatgta    240
acgtcacacg gtgaccacta tcattactat aatgggaaag ttccttatga tgccctcttt    300
agtgaagaac tcttgatgaa ggatccaaac tatcaactta agacgctga tattgtcaat    360 gaagtcaagg gtggttatat catcaaggtc gatggaaaat attatgtcta cctgaaagat    420
gcagctcatg ctgataatgt tcgaactaaa gatgaaatca atcgtcaaaa acaagaacat    480
gtcaaagata tgagaaggt taactctaat gttgctgtag caaggtctca gggacgatat    540
acgacaaatg atggttatgt ctttaatcca gctgatatta tcgaagatac gggtaatgct    600
tatatcgttc ctcatggagg tcactatcac tacattccca aaagcgattt atctgctagt    660
gaattagcag cagctaaagc acatctggct ggaaaaaata tgcaaccgag tcagttaagc    720
tattcttcaa cagctagtga caataacacg caatctgtag caaaaggatc aactagcaag    780
ccagcaaata aatctgaaaa tctccagagt cttttgaagg aactctatga ttcacctagc    840
gcccaacgtt acagtgaatc agatggcctg gtctttgacc ctgctaagat tatcagtcgt    900
acaccaaatg gagttgcgat tccgcatggc gaccattacc actttattcc ttacagcaag    960
ctttctgcct agaagaaaa gattgccaga atggtgccta tcagtggaac tggttctaca   1020
gtttctacaa atgcaaaacc taatgaagta gtgtctagtc taggcagtct ttcaagcaat   1080
ccttcttctt taacgacaag taaggagctc tcttcagcat ctgatggtta tattttaat    1140 ccaaaagata tcgttgaaga aacggctaca gcttatattg taagacatgg tgatcatttc   1200
cattacattc caaaatcaaa tcaaattggg caaccgactc ttccaaacaa tagtctagca   1260
acaccttctc catctcttcc aatcaatcca ggaacttcac atgagaaaca tgaagaagat   1320
ggatacggat tgatgctaa tcgtattatc gctgaagatg aatcaggttt tgtcatgagt   1380
cacggagacc acaatcatta tttcttcaag aaggacttga cagaagagca aattaaggtg   1440
cgcaaaaaca tttag                                                    1455

<210> SEQ ID NO 8
<211> LENGTH: 819
<212> TYPE: PRT
<213> ORGANISM: Streptococcus pneumoniae

<400> SEQUENCE: 8

Met Lys Ile Asn Lys Lys Tyr Leu Val Gly Ser Ala Ala Ala Leu Ile
  1               5                  10                  15

Leu Ser Val Cys Ser Tyr Glu Leu Gly Leu Tyr Gln Ala Arg Thr Val
```

```
                    20                      25                      30
Lys Glu Asn Asn Arg Val Ser Tyr Ile Asp Gly Lys Gln Ala Thr Gln
             35                      40                      45

Lys Thr Glu Asn Leu Thr Pro Asp Glu Val Ser Lys Arg Glu Gly Ile
     50                      55                      60

Asn Ala Glu Gln Ile Val Ile Lys Ile Thr Asp Gln Gly Tyr Val Thr
 65                      70                      75                      80

Ser His Gly Asp His Tyr His Tyr Tyr Asn Gly Lys Val Pro Tyr Asp
                     85                      90                      95

Ala Ile Ile Ser Glu Glu Leu Leu Met Lys Asp Pro Asn Tyr Lys Leu
                100                     105                     110

Lys Asp Glu Asp Ile Val Asn Glu Val Lys Gly Gly Tyr Val Ile Lys
                115                     120                     125

Val Asp Gly Lys Tyr Tyr Val Tyr Leu Lys Asp Ala Ala His Ala Asp
                130                     135                     140

Asn Val Arg Thr Lys Glu Glu Ile Asn Arg Gln Lys Gln Glu His Ser
145                     150                     155                     160

Gln His Arg Glu Gly Gly Thr Pro Arg Asn Asp Gly Ala Val Ala Leu
                    165                     170                     175

Ala Arg Ser Gln Gly Arg Tyr Thr Thr Asp Asp Gly Tyr Ile Phe Asn
                180                     185                     190

Ala Ser Asp Ile Ile Glu Asp Thr Gly Asp Ala Tyr Ile Val Pro His
                195                     200                     205

Gly Asp His Tyr His Tyr Ile Pro Lys Asn Glu Leu Ser Ala Ser Glu
                210                     215                     220

Leu Ala Ala Ala Glu Ala Phe Leu Ser Gly Arg Gly Asn Leu Ser Asn
225                     230                     235                     240

Ser Arg Thr Tyr Arg Arg Gln Asn Ser Asp Asn Thr Ser Arg Thr Asn
                    245                     250                     255

Trp Val Pro Ser Val Ser Asn Pro Gly Thr Thr Asn Thr Asn Thr Ser
                260                     265                     270

Asn Asn Ser Asn Thr Asn Ser Gln Ala Ser Gln Ser Asn Asp Ile Asp
                275                     280                     285

Ser Leu Leu Lys Gln Leu Tyr Lys Leu Pro Leu Ser Gln Arg His Val
                290                     295                     300

Glu Ser Asp Gly Leu Val Phe Asp Pro Ala Gln Ile Thr Ser Arg Thr
305                     310                     315                     320

Ala Arg Gly Val Ala Val Pro His Gly Asp His Tyr His Phe Ile Pro
                    325                     330                     335

Tyr Ser Gln Met Ser Glu Leu Glu Glu Arg Ile Ala Arg Ile Ile Pro
                340                     345                     350

Leu Arg Tyr Arg Ser Asn His Trp Val Pro Asp Ser Arg Pro Glu Gln
                355                     360                     365

Pro Ser Pro Gln Pro Thr Pro Glu Pro Ser Pro Gly Pro Gln Pro Ala
                370                     375                     380

Pro Asn Leu Lys Ile Asp Ser Asn Ser Ser Leu Val Ser Gln Leu Val
385                     390                     395                     400

Arg Lys Val Gly Glu Gly Tyr Val Phe Glu Glu Lys Gly Ile Ser Arg
                    405                     410                     415

Tyr Val Phe Ala Lys Asp Leu Pro Ser Glu Thr Val Lys Asn Leu Glu
                420                     425                     430

Ser Lys Leu Ser Lys Gln Glu Ser Val Ser His Thr Leu Thr Ala Lys
                435                     440                     445
```

```
Lys Glu Asn Val Ala Pro Arg Asp Gln Glu Phe Tyr Asp Lys Ala Tyr
    450                 455                 460

Asn Leu Leu Thr Glu Ala His Lys Ala Leu Phe Glu Asn Lys Gly Arg
465                 470                 475                 480

Asn Ser Asp Phe Gln Ala Leu Asp Lys Leu Leu Glu Arg Leu Asn Asp
                485                 490                 495

Glu Ser Thr Asn Lys Glu Lys Leu Val Asp Asp Leu Leu Ala Phe Leu
            500                 505                 510

Ala Pro Ile Thr His Pro Glu Arg Leu Gly Lys Pro Asn Ser Gln Ile
        515                 520                 525

Glu Tyr Thr Glu Asp Val Arg Ile Ala Gln Leu Ala Asp Lys Tyr
    530                 535                 540

Thr Thr Ser Asp Gly Tyr Ile Phe Asp Glu His Asp Ile Ile Ser Asp
545                 550                 555                 560

Glu Gly Asp Ala Tyr Val Thr Pro His Met Gly His Ser His Trp Ile
                565                 570                 575

Gly Lys Asp Ser Leu Ser Asp Lys Glu Lys Val Ala Ala Gln Ala Tyr
            580                 585                 590

Thr Lys Glu Lys Gly Ile Leu Pro Pro Ser Pro Asp Ala Asp Val Lys
        595                 600                 605

Ala Asn Pro Thr Gly Asp Ser Ala Ala Ile Tyr Asn Arg Val Lys
    610                 615                 620

Gly Glu Lys Arg Ile Pro Leu Val Arg Leu Pro Tyr Met Val Glu His
625                 630                 635                 640

Thr Val Glu Val Lys Asn Gly Asn Leu Ile Ile Pro His Lys Asp His
                645                 650                 655

Tyr His Asn Ile Lys Phe Ala Trp Phe Asp Asp His Thr Tyr Lys Ala
            660                 665                 670

Pro Asn Gly Tyr Thr Leu Glu Asp Leu Phe Ala Thr Ile Lys Tyr Tyr
        675                 680                 685

Val Glu His Pro Asp Glu Arg Pro His Ser Asn Asp Gly Trp Gly Asn
    690                 695                 700

Ala Ser Glu His Val Leu Gly Lys Lys Asp His Ser Glu Asp Pro Asn
705                 710                 715                 720

Lys Asn Phe Lys Ala Asp Glu Glu Pro Val Glu Thr Pro Ala Glu
                725                 730                 735

Pro Glu Val Pro Gln Val Glu Thr Glu Lys Val Glu Ala Gln Leu Lys
            740                 745                 750

Glu Ala Glu Val Leu Leu Ala Lys Val Thr Asp Ser Ser Leu Lys Ala
        755                 760                 765

Asn Ala Thr Glu Thr Leu Ala Gly Leu Arg Asn Asn Leu Thr Leu Gln
    770                 775                 780

Ile Met Asp Asn Ser Ile Met Ala Glu Ala Glu Lys Leu Leu Ala
785                 790                 795                 800

Leu Leu Lys Gly Ser Asn Pro Ser Ser Val Ser Lys Glu Lys Ile Asn
                805                 810                 815

Lys Leu Asn
```

<210> SEQ ID NO 9
<211> LENGTH: 2451
<212> TYPE: DNA
<213> ORGANISM: Streptococcus pneumoniae
<220> FEATURE:
<221> NAME/KEY: misc_feature -continued
<222> LOCATION: (1)..(2451)
<223> OTHER INFORMATION: n = a, c, t or g

<400> SEQUENCE: 9

| | | | | | |
|---|---|---|---|---|---|
| atgaaaatta | ataagaaata | ccttgttggt | tctgcggcag | ctttgatttt | aagtgtttgt | 60 |
| tcttacgagt | tgggactgta | tcaagctaga | acggttaagg | aaaataatcg | tgtttcctat | 120 |
| atagatggaa | acaagcgac | gcaaaaaacg | gagaatttga | ctcctgatga | ggttagcaag | 180 |
| cgtgaaggaa | tcaatgctga | gcaaatcgtc | atcaagataa | cagaccaagg | ctatgtcact | 240 |
| tcacatggcg | accactatca | ttattacaat | ggtaaggttc | cttatgacgc | tatcatcagt | 300 |
| gaagaattac | tcatgaaaga | tccaaactat | aagctaaaag | atgaggatat | tgttaatgag | 360 |
| gtcaagggtg | gatatgttat | caaggtagat | ggaaaatact | atgtttaccct | taaggatgct | 420 |
| gcccacgcgg | ataacgtccg | tacaaaagag | gaaatcaatc | gacaaaaaca | agagcatagt | 480 |
| caacatcgtg | aaggtggaac | tccaagaaac | gatggtgctg | ttgccttggc | acgttcgcaa | 540 |
| ggacgctata | ctacagatga | tggttatatc | tttaatgctt | ctgatatcat | agaggatact | 600 |
| ggtgatgctt | atatcgttcc | tcatggagat | cattaccatt | acattcctaa | gaatgagtta | 660 |
| tcagctagcg | agttggctgc | tgcagaagcc | ttcctatctg | gtcgaggaaa | tctgtcaaat | 720 |
| tcaagaaccct | atcgccgaca | aaatagcgat | aacacttcaa | gaacaaactg | ggtaccttct | 780 |
| gtaagcaatc | caggaactac | aaatactaac | acaagcaaca | acagcaacac | taacagtcaa | 840 |
| gcaagtcaaa | gtaatgacat | tgatagtctc | ttgaaacagc | tctacaaact | gcctttgagt | 900 |
| caacgacatg | tagaatctga | tggccttgtc | tttgatccag | cacaaatcac | aagtcgaaca | 960 |
| gctagaggtg | ttgcagtgcc | acacggagat | cattaccact | tcatcccctta | ctctcaaatg | 1020 |
| tctgaattgg | aagaacgaat | cgctcgtatt | attccccttc | gttatcgttc | aaaccattgg | 1080 |
| gtaccagatt | caaggccaga | acaaccaagt | ccacaaccga | ctccggaacc | tagtccaggc | 1140 |
| ccgcaacctg | caccaaatct | taaaatagac | tcaaattctt | ctttggttag | tcagctggta | 1200 |
| cgaaaagttg | gggaaggata | tgtattcgaa | gaaaagggca | tctctcgtta | tgtctttgcg | 1260 |
| aaagatttac | catctgaaac | tgttaaaaat | cttgaaagca | agttatcaaa | acaagagagt | 1320 |
| gtttcacaca | ctttaactgc | taaaaaagaa | aatgttgctc | ctcgtgacca | agaattttat | 1380 |
| gataaagcat | ataatctgtt | aactgaggct | cataaagcct | tgtttgnaaa | taagggtcgt | 1440 |
| aattctgatt | ccaagccctt | agacaaatta | ttagaacgct | tgaatgatga | atcgactaat | 1500 |
| aaagaaaaat | tggtagatga | tttattggca | ttcctagcac | caattaccca | tccagagcga | 1560 |
| cttggcaaac | caaattctca | aattgagtat | actgaagacg | aagttcgtat | tgctcaatta | 1620 |
| gctgataagt | atacaacgtc | agatggttac | atttttgatg | aacatgatat | aatcagtgat | 1680 |
| gaaggagatg | catatgtaac | gcctcatatg | ggccatagtc | actggattgg | aaaagatagc | 1740 |
| ctttctgata | aggaaaaagt | tgcagctcaa | gcctatacta | agaaaaagg | tatcctacct | 1800 |
| ccatctccag | acgcagatgt | taaagcaaat | ccaactggag | atagtgcagc | agctatttac | 1860 |
| aatcgtgtga | agggggaaaa | acgaattcca | ctcgttcgac | ttccatatat | ggttgagcat | 1920 |
| acagttgagg | ttaaaaacgg | taatttgatt | attcctcata | aggatcatta | ccataatatt | 1980 |
| aaatttgctt | ggtttgatga | tcacacatac | aaagctccaa | atggctatac | cttggaagat | 2040 |
| ttgtttgcga | cgattaagta | ctacgtagaa | caccctgacg | aacgtccaca | ttctaatgat | 2100 |
| ggatggggca | atgccagtga | gcatgtgtta | ggcaagaaag | accacagtga | agatccaaat | 2160 |
| aagaacttca | aagcggatga | agagccagta | gaggaaacac | ctgctgagcc | agaagtccct | 2220 |

-continued

```
caagtagaga ctgaaaaagt agaagcccaa ctcaaagaag cagaagtttt gcttgcgaaa    2280
gtaacggatt ctagtctgaa agccaatgca acagaaactc tagctggttt acgaaataat    2340
ttgactcttc aaattatgga taacaatagt atcatggcag aagcagaaaa attacttgcg    2400
ttgttaaaag gaagtaatcc ttcatctgta agtaaggaaa aaataaacta a             2451
```

<210> SEQ ID NO 10
<211> LENGTH: 819
<212> TYPE: PRT
<213> ORGANISM: Streptococcus pneumoniae

<400> SEQUENCE: 10

```
Met Lys Ile Asn Lys Lys Tyr Leu Ala Gly Ser Val Ala Val Leu Ala
 1               5                  10                  15

Leu Ser Val Cys Ser Tyr Glu Leu Gly Arg Tyr Gln Ala Gly Gln Asp
                20                  25                  30

Lys Lys Glu Ser Asn Arg Val Ala Tyr Ile Asp Gly Asp Gln Ala Gly
            35                  40                  45

Gln Lys Ala Glu Asn Leu Thr Pro Asp Glu Val Ser Lys Arg Glu Gly
        50                  55                  60

Ile Asn Ala Glu Gln Ile Val Lys Ile Thr Asp Gln Gly Tyr Val
 65                  70                  75                  80

Thr Ser His Gly Asp His Tyr His Tyr Tyr Asn Gly Lys Val Pro Tyr
                85                  90                  95

Asp Ala Ile Ile Ser Glu Glu Leu Leu Met Lys Asp Pro Asn Tyr Gln
            100                 105                 110

Leu Lys Asp Ser Asp Ile Val Asn Glu Ile Lys Gly Gly Tyr Val Ile
        115                 120                 125

Lys Val Asn Gly Lys Tyr Tyr Val Tyr Leu Lys Asp Ala Ala His Ala
    130                 135                 140

Asp Asn Ile Arg Thr Lys Glu Glu Ile Lys Arg Gln Lys Gln Glu Arg
145                 150                 155                 160

Ser His Asn His Asn Ser Arg Ala Asp Asn Ala Val Ala Ala Ala Arg
                165                 170                 175

Ala Gln Gly Arg Tyr Thr Thr Asp Asp Gly Tyr Ile Phe Asn Ala Ser
            180                 185                 190

Asp Ile Ile Glu Asp Thr Gly Asp Ala Tyr Ile Val Pro His Gly Asp
        195                 200                 205

His Tyr His Tyr Ile Pro Lys Asn Glu Leu Ser Ala Ser Glu Leu Ala
    210                 215                 220

Ala Ala Glu Ala Tyr Trp Asn Gly Lys Gln Gly Ser Arg Pro Ser Ser
225                 230                 235                 240

Ser Ser Ser Tyr Asn Ala Asn Pro Ala Gln Pro Arg Leu Ser Glu Asn
                245                 250                 255

His Asn Leu Thr Val Thr Pro Thr Tyr His Gln Asn Gln Gly Glu Asn
            260                 265                 270

Ile Ser Ser Leu Leu Arg Glu Leu Tyr Ala Lys Pro Leu Ser Glu Arg
        275                 280                 285

His Val Glu Ser Asp Gly Leu Ile Phe Asp Pro Ala Gln Ile Thr Ser
    290                 295                 300

Arg Thr Ala Arg Gly Val Ala Val Pro His Gly Asn His Tyr His Phe
305                 310                 315                 320

Ile Pro Tyr Glu Gln Met Ser Glu Leu Glu Lys Arg Ile Ala Arg Ile
                325                 330                 335
```

```
Ile Pro Leu Arg Tyr Arg Ser Asn His Trp Val Pro Asp Ser Arg Pro
        340                 345                 350

Glu Glu Pro Ser Pro Gln Pro Thr Pro Glu Pro Ser Pro Ser Pro Gln
        355                 360                 365

Pro Ala Pro Ser Asn Pro Ile Asp Gly Lys Leu Val Lys Glu Ala Val
        370                 375                 380

Arg Lys Val Gly Asp Gly Tyr Val Phe Glu Glu Asn Gly Val Ser Arg
385                 390                 395                 400

Tyr Ile Pro Ala Lys Asp Leu Ser Ala Glu Thr Ala Ala Gly Ile Asp
                405                 410                 415

Ser Lys Leu Ala Lys Gln Glu Ser Leu Ser His Lys Leu Gly Thr Lys
                420                 425                 430

Lys Thr Asp Leu Pro Ser Ser Asp Arg Glu Phe Tyr Asn Lys Ala Tyr
                435                 440                 445

Asp Leu Leu Ala Arg Ile His Gln Asp Leu Leu Asp Asn Lys Gly Arg
            450                 455                 460

Gln Val Asp Phe Glu Ala Leu Asp Asn Leu Leu Glu Arg Leu Lys Asp
465                 470                 475                 480

Val Ser Ser Asp Lys Val Lys Leu Val Glu Asp Ile Leu Ala Phe Leu
                485                 490                 495

Ala Pro Ile Arg His Pro Glu Arg Leu Gly Lys Pro Asn Ala Gln Ile
                500                 505                 510

Thr Tyr Thr Asp Asp Glu Ile Gln Val Ala Lys Leu Ala Gly Lys Tyr
                515                 520                 525

Thr Ala Glu Asp Gly Tyr Ile Phe Asp Pro Arg Asp Ile Thr Ser Asp
            530                 535                 540

Glu Gly Asp Ala Tyr Val Thr Pro His Met Thr His Ser His Trp Ile
545                 550                 555                 560

Lys Lys Asp Ser Leu Ser Glu Ala Glu Arg Ala Ala Ala Gln Ala Tyr
                565                 570                 575

Ala Glu Glu Lys Gly Leu Thr Pro Pro Ser Thr Asp His Gln Asp Ser
                580                 585                 590

Gly Asn Thr Glu Ala Lys Gly Ala Glu Ala Ile Tyr Asn Arg Val Lys
            595                 600                 605

Ala Ala Lys Lys Val Pro Leu Asp Arg Met Pro Tyr Asn Leu Gln Tyr
            610                 615                 620

Thr Val Glu Val Lys Asn Gly Ser Leu Ile Ile Pro His Tyr Asp His
625                 630                 635                 640

Tyr His Asn Ile Lys Phe Glu Trp Phe Asp Glu Gly Leu Tyr Glu Ala
                645                 650                 655

Pro Lys Gly Tyr Thr Leu Glu Asp Leu Leu Ala Thr Val Lys Tyr Tyr
                660                 665                 670

Val Glu His Pro Asn Glu Arg Pro His Ser Asp Asn Gly Phe Gly Asn
                675                 680                 685

Ala Ser Asp His Val Gln Arg Asn Lys Asn Gly Gln Ala Asp Thr Asn
            690                 695                 700

Gln Thr Glu Lys Pro Ser Glu Lys Pro Gln Thr Glu Lys Pro Glu
705                 710                 715                 720

Glu Glu Thr Pro Arg Glu Glu Lys Pro Gln Ser Glu Lys Pro Glu Ser
                725                 730                 735

Pro Lys Pro Thr Glu Glu Pro Glu Glu Ser Pro Glu Glu Ser Glu Glu
                740                 745                 750
```

```
         Pro Gln Val Glu Thr Glu Lys Val Glu Glu Lys Leu Arg Glu Ala Glu
                 755                 760                 765

Asp Leu Leu Gly Lys Ile Gln Asp Pro Ile Ile Lys Ser Asn Ala Lys
                 770                 775                 780

Glu Thr Leu Thr Gly Leu Lys Asn Asn Leu Leu Phe Gly Thr Gln Asp
         785                 790                 795                 800

Asn Asn Thr Ile Met Ala Glu Ala Glu Lys Leu Leu Ala Leu Leu Lys
                         805                 810                 815

Glu Ser Lys

<210> SEQ ID NO 11
         <211> LENGTH: 2531
         <212> TYPE: DNA
         <213> ORGANISM: Streptococcus pneumoniae

<400> SEQUENCE: 11
atgaaaatta taaaaaata tctagcaggt tcagtggcag tccttgccct aagtgtttgt      60
tcctatgagc ttggacgtta ccaagctggt caggataaga aagagtctaa tcgagttgct     120
tatatagatg tgatcaggc tggtcaaaag gcagaaaact tgacaccaga tgaagtcagt     180
aagagggagg ggatcaacgc cgaacaaatt gttatcaaga ttacggatca aggttatgtg     240
acctctcatg gagaccatta tcattactat aatggcaagg ttccttatga tgccatcatc     300
agtgaagagc tcctcatgaa agatccgaat tatcagttga aggattcaga cattgtcaat     360
gaaatcaagg gtggttatgt cattaaggta acggtaaat actatgttta ccttaaggat      420
gcrgctcatg cggataatat tcggacaaaa gaagagatta acgtcagaa gcaggaacgc      480 agtcataatc ataactcaag agcagataat gctgttgctg cagccagagc ccaaggacgt     540
tatacaacgg atgatgggta tcttcaat gcatctgata tcattgagga cacgggtgat      600
gcttatatcg ttcctcacgg cgaccattac cattacattc ctaagaatga gttatcagct     660
agcgagttag ctgctgcaga agcctattgg aatgggaagc agggatctcg tccttcttca     720
agttctagtt ataatgcaaa tccagctcaa ccaagattgt cagagaacca caatctgact     780
gtcactccaa cttatcatca aaatcaaggg gaaaacattt caagcctttt acgtgaattg     840
tatgctaaac cctttatcaga acgccatgtg aatctgatg gccttatttt cgacccagcg      900
caaatcacaa gtcgaaccgc cagaggtgta gctgtccctc atggtaacca ttaccacttt     960
atcccttatg aacaaatgtc tgaattggaa aaacgaattg ctcgtattat tcccccttcgt    1020 tatcgttcaa accattgggt accagattca agaccagaag aaccaagtcc acaaccgact    1080
ccagaaccta gtccaagtcc gcaaccagcc ccaagcaatc caattgatgg gaaattggtc    1140
aaagaagctg ttcgaaaagt aggcgatggt tatgtctttg aggagaatgg agtttctcgt    1200
tatatcccag ccaaggatct ttcagcagaa acagcagcag gcattgatag caaactggcc    1260
aagcaggaaa gttatatctca taagctagga actaagaaaa ctgacctccc atctagtgat    1320
cgagaatttt acaataaggc ttatgactta ctagcaagaa ttcaccaaga tttacttgat    1380
aataaaggtc gacaagttga ttttgaggct ttggataacc tgttggaacg actcaaggat    1440
gtctcaagtg ataaagtcaa gttagtggaa gatattcttg ccttcttagc tccgattcgt    1500
catccagaac gtttaggaaa accaaatgcg caaattacct acactgatga tgagattcaa    1560
gtagccaagt ggcaggcaa gtacacagca gaagacggtt atatctttga tcctcgtgat    1620
ataaccagtg atgaggggga tgcctatgta actccacata tgacccatag ccactggatt    1680
aaaaaagata gtttgtctga agctgagaga gcggcagccc aggcttatgc traagagaaa    1740
```

```
ggtttgaccc ctccttcgac agaccatcag gattcaggaa atactgaggc aaaaggagca    1800
gaagctatct acaaccgmgt gaaagcagct aagaaggtgc cacttgatcg tatgccttac    1860
aatcttcaat atactgtaga agtcaaaaac ggtagtttaa tcatacctca ttatgaccat    1920
taccataaca tcaaatttga gtggtttgac gaaggccttt atgaggcacc taaggggtat    1980
actcttgagg atcttttggc gactgtcaag tactatgtcg aacatccaaa cgaacgtccg    2040
cattcagata atggttttgg taacgctagc gaccatgttc aaagaaacaa aaatggtcaa    2100
gctgatacca atcaaacgga aaaccaagc gaggagaaac ctcagacaga aaaacctgag     2160
gaagaaaccc ctcgagaaga gaaaccgcaa agcgagaaac cagagtctcc aaaaccaaca    2220
gaggaaccag aagaatcacc agaggaatca gaagaacctc aggtcgagac tgaaaaggtt    2280
gaagaaaaac tgagagaggc tgaagattta cttggaaaaa tccaggatcc aattatcaag    2340
tccaatgcca aagagactct cacaggatta aaaaataatt tactatttgg cacccaggac    2400
aacaatacta ttatggcaga agctgaaaaa ctattggctt tattaaagga gagtaagtaa    2460
aggtagaagc ttaagggcga atttggcacc caggacaaca atactattat ggcagaagct    2520
gaaaaactat t                                                         2531

<210> SEQ ID NO 12
<211> LENGTH: 6
<212> TYPE: PRT
<213> ORGANISM: Artificial Sequence
<220> FEATURE:
<221> NAME/KEY: VARIANT
<222> LOCATION: (1)..(6)
<223> OTHER INFORMATION: Xaa = any amino acid

<400> SEQUENCE: 12

His Xaa Xaa His Xaa His
 1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Substrate
      sequence for Type II Signal Peptidase.

<400> SEQUENCE: 13

Leu Ser Val Cys
 1

<210> SEQ ID NO 14
<211> LENGTH: 4
<212> TYPE: PRT
<213> ORGANISM: Artificial Sequence
<220> FEATURE:
<221> NAME/KEY: VARIANT
<222> LOCATION: (2)..(3)
<223> OTHER INFORMATION: Xaa = any amino acid

<400> SEQUENCE: 14

Leu Xaa Xaa Cys
 1
```

VACCINE COMPOSITIONS COMPRISING STREPTOCOCCUS PNEUMONIAE POLYPEPTIDES HAVING SELECTED STRUCTURAL MOTIFS

This application is a divisional of U.S. application Ser. No. 09/468,656, filed 21 Dec. 1999, now U.S. Pat. No. 6,582,706, which is based on U.S. Provisional Application No. 60/113,048, filed 21 Dec. 1998, the disclosures of which are hereby incorporated by reference in their entirety.

FIELD OF THE INVENTION

This invention relates generally to the field of bacterial antigens and their use, for example, as immunogenic agents in humans and animals to stimulate an immune response. More specifically, it relates to the vaccination of mammalian species with a polypeptide comprising at least one conserved histidine triad residue (HxxHxH - SEQ ID NO: 12) and at least one helix-forming polypeptide obtained from *Streptococcus pneumoniae* as a mechanism for stimulating production of antibodies that protect the vaccine recipient against infection by a wide range of serotypes of pathogenic *S. pneumoniae*. Further, the invention relates to antibodies against such polypeptides useful in diagnosis and passive immune therapy with respect to diagnosing and treating such pneumococcal infections.

In a particular aspect, the present invention relates to the prevention and treatment of pneumococcal infections such as infections of the middle ear, nasopharynx, lung and bronchial areas, blood, CSF, and the like, that are caused by pneumococcal bacteria.

BACKGROUND OF THE INVENTION

*Streptococcus pneumoniae* is a gram positive bacteria which is a major causative agent in invasive infections in animals and humans, such as sepsis, meningitis, otitis media and lobar pneumonia (Tuomanen et al. *New Engl. J. Med.* 322:1280–1284 (1995)). As part of the infective process, pneumococci readily bind to non-inflamed human epithelial cells of the upper and lower respiratory tract by binding to eukaryotic carbohydrates in a lectin-like manner (Cundell et al., *Micro. Path.* 17:361–374 (1994)). Conversion to invasive pneumococcal infections for bound bacteria may involve the local generation of inflammatory factors which may activate the epithelial cells to change the number and type of receptors on their surface (Cundell et al., *Nature,* 377:435–438 (1995)). Apparently, one such receptor, platelet activating factor (PAF) is engaged by the pneumococcal bacteria and within a very short period of time (minutes) from the appearance of PAF, pneumococci exhibit strongly enhanced adherence and invasion of tissue. Certain soluble receptor analogs have been shown to prevent the progression of pneumococcal infections (Idanpaan-Heikkila et al., *J. Inf. Dis.,* 176:704–712 (1997)). A number of various other proteins have been suggested as being involved in the pathogenicity of *S. pneumoniae*. There remains a need for identifying polypeptides having epitopes in common from various strains of *S. pneumoniae* in order to utilize such polypeptides as vaccines to provide protection against a wide variety of *S. pneumoniae*.

SUMMARY OF INVENTION

In accordance with the present invention, there is provided vaccines and vaccine compositions that include polypeptides obtained from *S. pneumoniae* and/or variants of said polypeptides and/or active fragments of such polypeptides.

The active fragments, as hereinafter defined, include a histidine triad residue(s) and/or coiled coil regions of such polypeptides.

The term "percent identity" or "percent identical," when referring to a sequence, means that a sequence is compared to a claimed or described sequence from an alignment of the sequence to be compared (the "Compared Sequence") with the described or claimed sequence (the "Reference Sequence"). The percent identity is determined as follows:

Percent Identity=[1-(C/R)]100 wherein C is the number of differences between the Reference Sequence and the Compared Sequence over the length of the alignment between the Compared Sequence and the Reference Sequence wherein (i) each base or amino acid in the Reference Sequence that does not have an aligned base or amino acid in the Compared Sequence and (ii) each gap in the Reference Sequence and (iii) each aligned base or amino acid in the Reference Sequence that is different from an aligned base or amino acid in the Compared Sequence, each being a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence in which the Percent Identity as calculated above is about equal to or greater than a specified minimum Percent Identity then the Compared Sequence has the specified minimum Percent Identity to the Reference Sequence even though alignments may exist in which the herein above calculated Percent Identity is less than the specified Percent Identity.

"Isolated" in the context of the present invention with respect to polypeptides and/or polynucleotides means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment. The polypeptides and polynucleotides of the present invention are preferably provided in an isolated form, and preferably are purified to homogeneity.

BRIEF DESCRIPTION OF DRAWINGS

FIG. 2A shows that one hundred percent of the mice immunized with the SP36 antiserum survived the 21-day observation period after challenge with 172 CFU of strain SJ2 (serotype 6B). Eighty percent of the mice immunized with a control serum (rabbit anti-FimC) died by day 8, and ninety percent died by day 12. FIG. 2B shows that 90 percent of the mice immunized with the Sp36 antiserum survived the 8-day observation after challenge with 862 CFU of strain EF6796 (serotype 6A). Ninety percent of the mice immunized with a control serum (collected before immunization) died by day 5.

FIG. 6 is an amino acid alignment comparison of four related pneumococcal proteins, namely Sp36A (PhtA; SEQ ID NO:8), Sp36B (PhtB; SEQ ID NO:10), Sp36D (PhtD; SEQ ID NO:4), Sp36E (PhtE; SEQ ID NO:6), respectively. Dashes in a sequence indicate gaps introduced to maximize the sequence similarity. Amino acid residues that match are boxed.

Figure 7C:
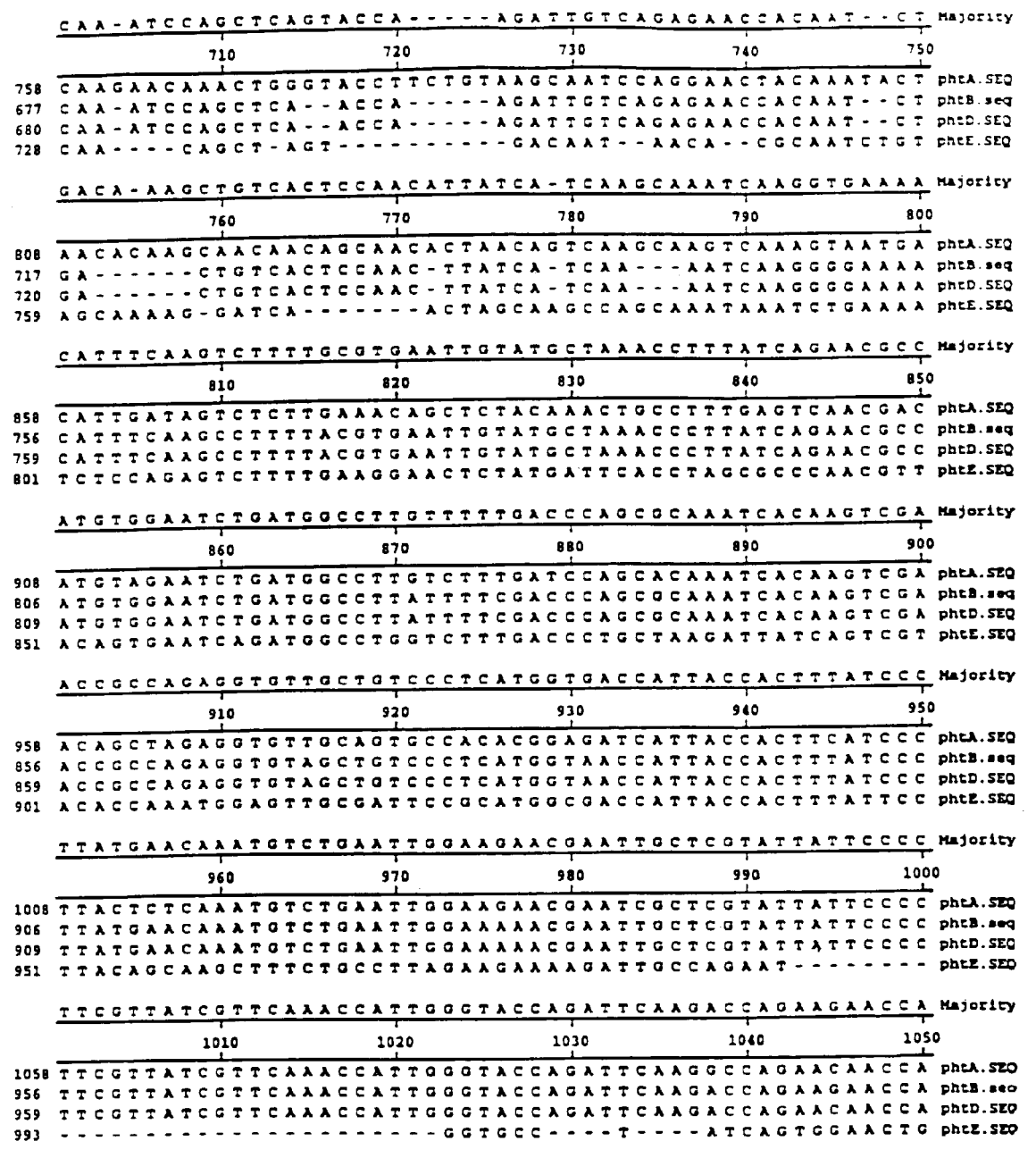
Figure 7E:
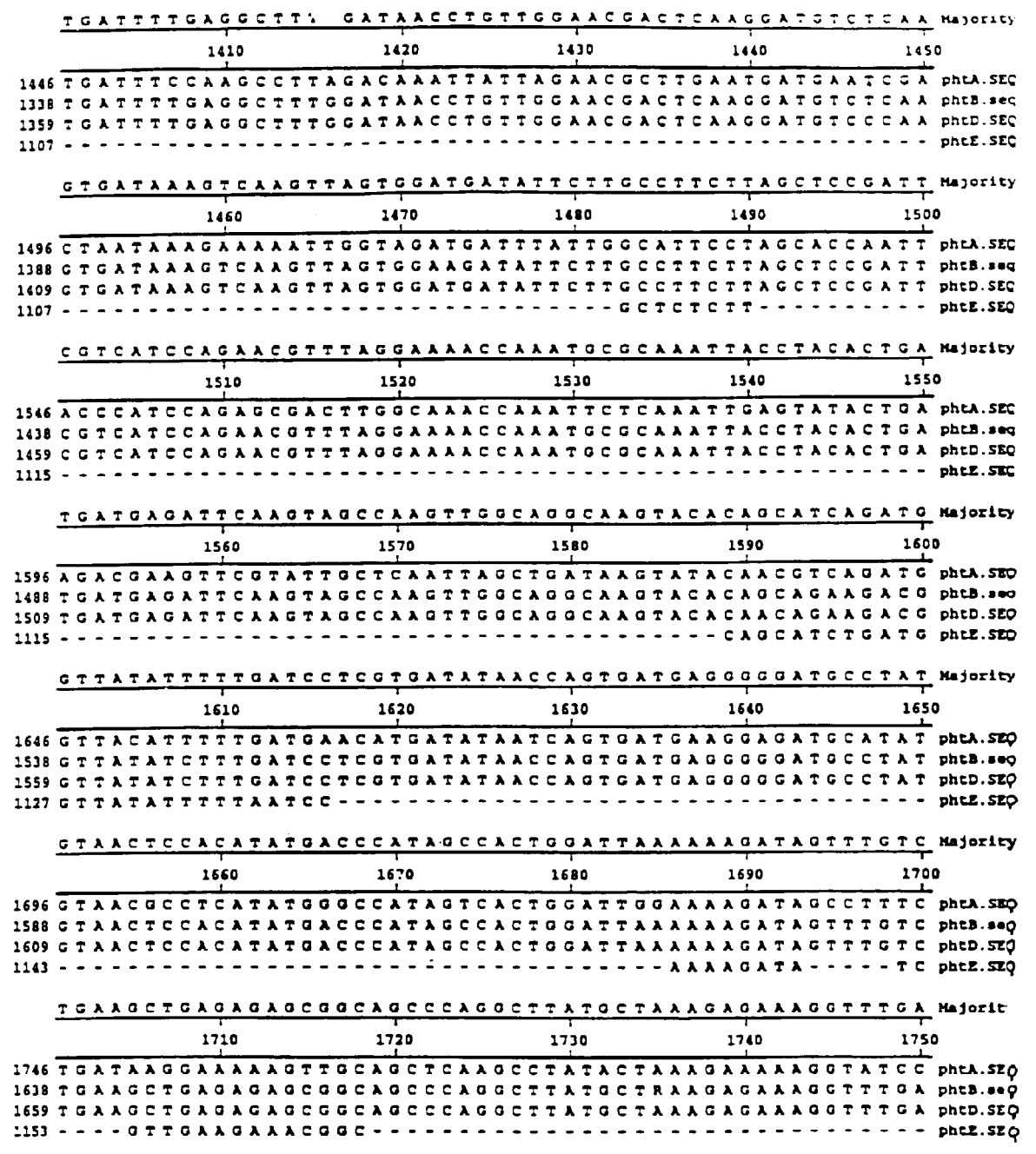
Figure 7F:
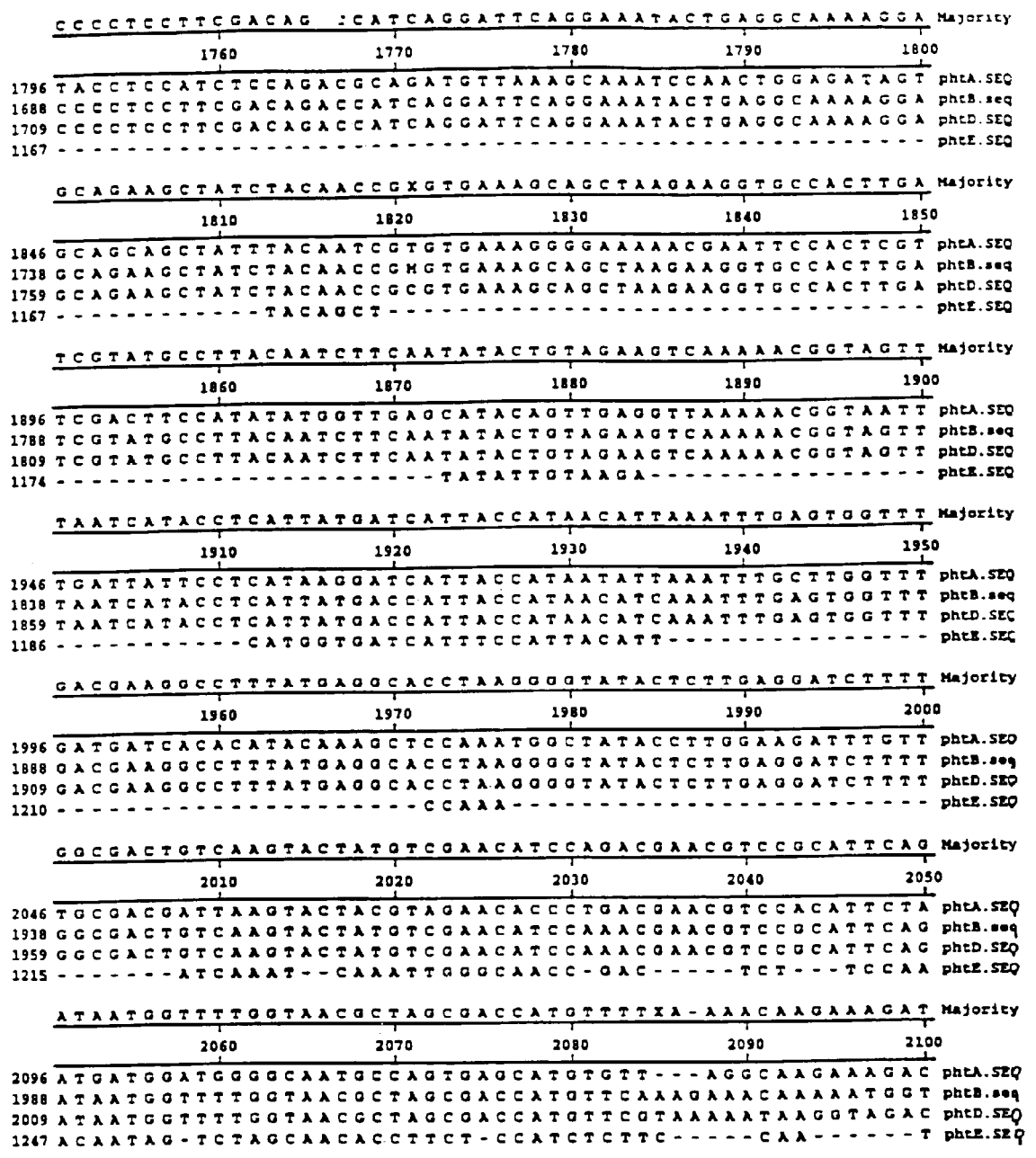
Figure 7G:
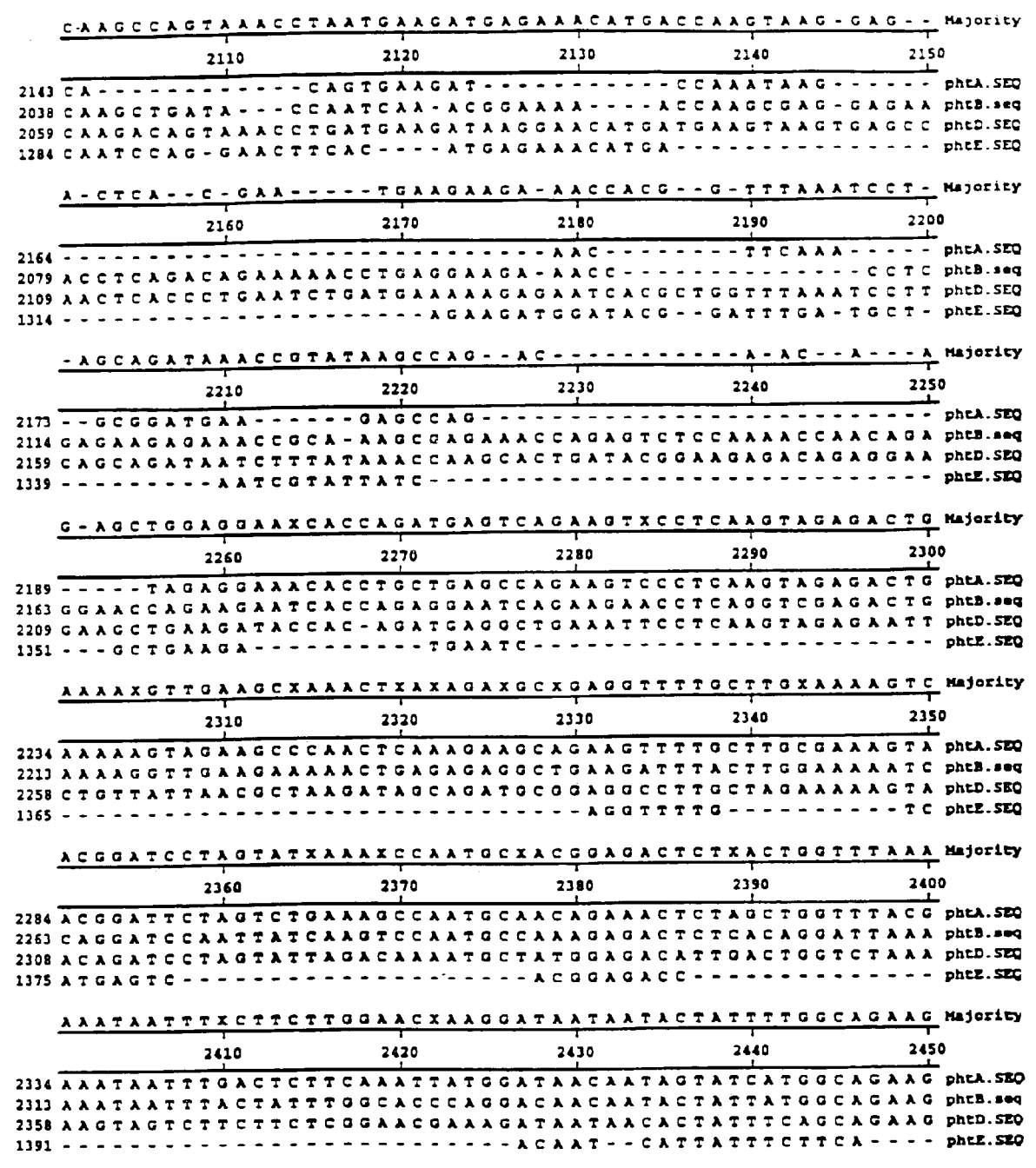

FIG. 7 is a nucleotide alignment comparison of four related pneumococcal genes, namely Sp36A (PhtA; SEQ ID NO:9), Sp36B (PhtB; SEQ ID NO:11), Sp36D (PhtD; SEQ ID NO:5), Sp36E (PhtE; SEQ ID NO:7), respectively. Dashes in a sequence indicate gaps introduced to maximize the sequence similarity.

SUMMARY OF THE INVENTION

Figure 1:
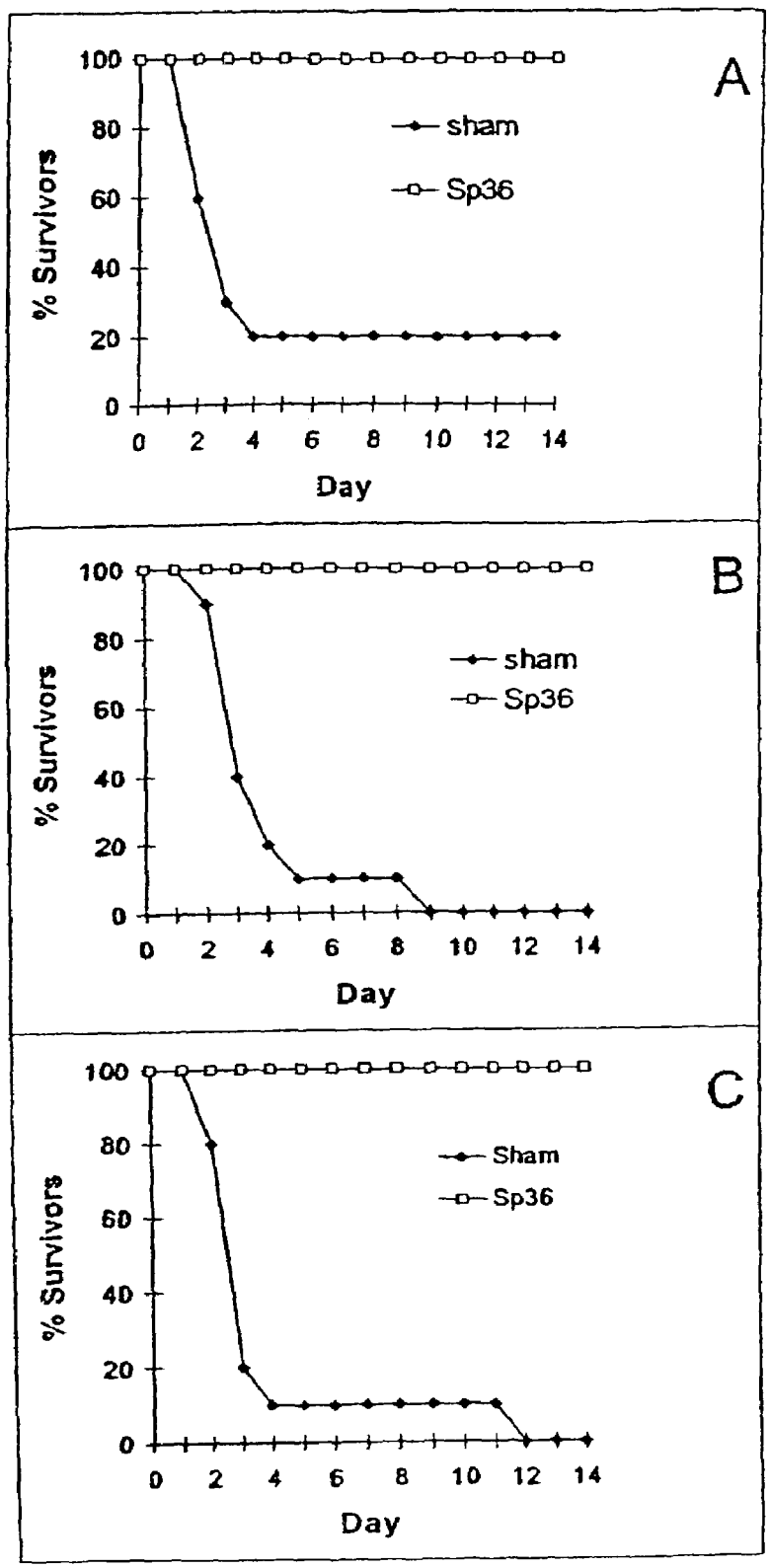
FIGS. 1A–1C, respectively, report the results of three experiments using different preparations of SP36. The results demonstrate that active immunization with recombinant SP36 derived from pneumococcal strain Norway serotype 4 is able to protect mice from death in a model of pneumococcal sepsis using a heterologous strain, SJ2 (serotype 6B). In each of the three experiments shown, one hundred percent of the mice immunized with SP36 survived for the 14-day observation period following challenge with approximately 500 cfu of pneumococci, while eighty to one hundred percent of sham-immunized mice (injected with PBS and adjuvant) died during the same period.

In accordance with one aspect of the present invention, there is provided a vaccine, generally in the form of a composition, that includes at least one polypeptide that is at least 90% identical to (c) a polypeptide sequence comprising amino acids 20–838 of SEQ ID NO:4 or (ii) a polypeptide sequence comprising amino acids 480 of SEQ ID NO:6 or an active fragment of the foregoing.

In accordance with another aspect of the present invention, there is provided a vaccine, generally in the form of a composition, that includes an active fragment of a polypeptide that is at least 90% identical to (i) a polypeptide comprising amino acids 20–819 of SEQ ID NO:8 or (ii) a polypeptide comprising amino acids 20–819 of SEQ ID NO:10.

The term "active fragment" means a fragment that includes one or more histidine triad residues and/or one or more coiled coil regions. A "histidine triad residue" is the portion of the polypeptide that has the sequence HxxHxH (SEQ ID NO: 12) wherein H is histidine and x is an amino acid other than histidine A coiled coil region is the region predicted by "Coils" algorithm: Lupas, A., Van Dyke, M., and Stock, J. (1991) Predicting Coiled Coils from Protein Sequences, *Science* 252:1162–1164.

In accordance with one embodiment, the active fragment includes both one or more histidine triad residues and at least one coiled coil region of the applicable polypeptide sequence. In accordance with another embodiment, the active fragment includes at least two histidine triad residues.

In another embodiment, the active fragment that includes at least one histidine triad residue or at least one coiled-coil region of the applicable polypeptide includes at least about ten percent of the applicable polypeptide and no more than about 85% of the applicable polypeptide.

The polypeptide of SEQ ID NO:4 includes five histidine triad residues, as follows: amino acids 83–88, 207–212, 315–320, 560–565, and 644–649.

The polypeptide of SEQ ID NO:6 includes five histidine triad residues, as follows: amino acids 83–88, 205–210, 309–314, 396–401, and 461–466.

In addition, the polypeptide of SEQ ID NO:4 includes two coiled-coil regions (amino acids 139–159 and amino acids 769–791) and the polypeptide of SEQ ID NO:6 includes one coiled-coil region (amino acids 139–172).

The polypeptide of SEQ ID NO: 8 includes the following regions:

HxxHxH (SEQ ID NO: 12): amino acids 82–87, 208–213, 328–333, 569–574, and 653–658.

Coiled-coils: amino acids 137–164, 425–453, 481–512, and 743–770.

A vaccine, or vaccine composition, in accordance with the present invention may include one or more of the herein above described polypeptides or active fragments thereof. When employing more than one polypeptide or active fragment, such two or more polypeptides and/or active fragments may be used as a physical mixture or as a fusion of two or more polypeptides or active fragments. The fusion fragment or fusion polypeptide may be produced, for example, by recombinant techniques or by the use of appropriate linkers for fusing previously prepared polypeptides or active fragments.

In an embodiment of the invention, there is provided (a) a polypeptide that is at least 95% identical or at least 97% identical or 100% identical to (i) a polypeptide sequence comprising amino acids 20–838 of SEQ ID NO:4 or (ii) a polypeptide sequence comprising amino acids 21–480 of SEQ ID NO:6 or (b) an active fragment of the polypeptide of (a).

In the case where the polypeptide is a variant of the polypeptide comprising the mature polypeptide of SEQ ID NO:4 or SEQ ID NO:6, or any of the active fragments of the invention, the variation in the polypeptide or fragment is generally in a portion thereof other than the histidine triad residues and the coiled-coil region, although variations in one or more of these regions may be made.

In many cases, the variation in the polypeptide or active fragment is a conservative amino acid substitution, although other substitutions are within the scope of the invention.

In accordance with the present invention, a polypeptide variant includes variants in which one or more amino acids are substituted and/or deleted and/or inserted.

In another aspect, the invention relates to passive immunity vaccines formulated from antibodies against a polypeptide or active fragment of a polypeptide of the present invention. Such passive immunity vaccines can be utilized to prevent and/or treat pneumococcal infections in patients. In this manner, according to a further aspect of the invention, a vaccine can be produced from a synthetic or recombinant polypeptide of the present invention or an antibody against such polypeptide.

In still another aspect the present invention relates to a method of using one or more antibodies (monoclonal, polyclonal or sera) to the polypeptides of the invention as described above for the prophylaxis and/or treatment of diseases that are caused by pneumococcal bacteria. In particular, the invention relates to a method for the prophylaxis and/or treatment of infectious diseases that are caused by *S. pneumoniae*. In a still further preferred aspect, the invention relates to a method for the prophylaxis and/or treatment of otitis media, nasopharyngeal, bronchial infections, and the like in humans by utilizing a vaccine of the present invention.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutical carriers are generally added that are compatible with the active ingredients and acceptable for pharmaceutical use. Examples of such carriers include, but are not limited to, water, saline solutions, dextrose, or glycerol. Combinations of carriers may also be used.

Vaccine compositions may further incorporate additional substances to stabilize pH, or to function as adjuvants, wetting agents, or emulsifying agents, which can serve to improve the effectiveness of the vaccine.

Vaccines are generally formulated for parental administration and are injected either subcutaneously or intramuscularly. Such vaccines can also be formulated as suppositories or for oral administration, using methods known in the art.

The amount of vaccine sufficient to confer immunity to pathogenic bacteria is determined by methods well known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 50 to 500 µg purified protein may be given.

The present invention is also directed to a vaccine in which a polypeptide or active fragment of the present invention is delivered or administered in the form of a polynucleotide encoding the polypeptide or active fragment, whereby the polypeptide or active fragment is produced in vivo. The polynucleotide may be included in a suitable expression vector and combined with a pharmaceutically acceptable carrier.

In addition, the polypeptides of the present invention can be used as immunogens to stimulate the production of antibodies for use in passive immunotherapy, for use as diagnostic reagents, and for use as reagents in other processes such as affinity chromatography.

In another aspect the present invention provides polynucleotides which encode the herein above described polypeptides and active fragments of the invention. The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand.

In accordance with another aspect of the present invention, there is provided (A) an isolated polynucleotide that is at least 90% identical to a polynucleotide sequence encoding (i) a polypeptide comprising amino acids 20–838 of SEQ ID NO:4 or (ii) a polypeptide comprising amino acids 21–480 of SEQ ID NO:6, or (B) a fragment of the polynucleotide of (A) that encodes an active polypeptide fragment or (C) a polynucleotide that is at least 90% identical to a polynucleotide sequence encoding an active fragment of (i) a polypeptide comprising amino acids 20–819 of SEQ ID NO:8 or (ii) a polypeptide comprising amino acids 20–819 of SEQ ID NO:10.

In specific embodiments, the polynucleotide is at least 95% identical, preferably at least 97% identical, and even 100% identical to such polynucleotide sequence.

The term "polynucleotide encoding a polypeptide" encompasses a polynucleotide which includes only coding sequence for the polypeptide as well as a polynucleotide which includes additional coding and/or non-coding sequence.

The present invention further relates to variants of polynucleotides. The variants of the polynucleotides may be a naturally occurring allelic variant of the polynucleotides or a non-naturally occurring variant of the polynucleotides. The variants include variants in which one or more bases are substituted, deleted or inserted. Complements to such coding polynucleotides may be utilized to isolate polynucleotides encoding the same or similar polypeptides. In particular, such procedures are useful to obtain native immunogenic portions of polypeptides from different serotypes of *S. pneumoniae*, which is especially useful in the production of "chain" polypeptide vaccines containing multiple immunogenic segments.

SEQ ID NO:5 is a representative example of a polynucleotide encoding the polypeptide of SEQ ID NO:4 and SEQ ID NO:7 is a representative example of a polynucleotide encoding the polypeptide of SEQ ID NO:6. SEQ ID NO:9 is a representative example of a polynucleotide encoding the polypeptide of SEQ ID NO:8, and SEQ ID NO:11 is a representative example of a polynucleotide encoding the polypeptide of SEQ ID NO:10. As a result of the known degeneracy of the genetic code, other polynucleotides that encode the polypeptides of SEQ ID NO:4, SEQ ID NO:6, SEQ ID NO:8 and SEQ ID NO:10 should be apparent to those skilled in the art from the teachings herein.

The polynucleotides encoding the immunogenic polypeptides described above may also have the coding sequence fused in frame to a marker sequence which allows for purification of the polypeptides of the present invention. The marker sequence may be, for example, a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention also relates to vectors which include polynucleotides encoding one or more of the polypeptides of the invention, host cells which are genetically engineered with vectors of the invention and the production of such immunogenic polypeptides by recombinant techniques in an isolated and substantially immunogenically pure form.

Host cells are genetically engineered (transduced or transformed or transfected) with the vectors comprising a polynucleotide encoding a polypeptide of the invention. The vector may be, for example, in the form of a plasmid, a viral particle, a phage, etc. The engineered host cells can be cultured in conventional nutrient media modified as appropriate for activating promoters, selecting transformants or amplifying the polynucleotides which encode such polypeptides. The culture conditions, such as temperature, pH and the like, are those previously used with the host cell selected for expression, and will be apparent to the ordinarily skilled artisan.

Vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as herein above described, as well as an appropriate promoter or control sequence, may be employed to transform an appropriate host to permit the host to express the proteins.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen, Inc.), pbs, pD10, phagescript, psiX174, pbluescript SK, pbsks, pNH8A, pNH16a, pNH18A, pNH46A (Stratagene); ptrc99a, pKK223–3, pKK233–3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232–8 and pCM7. Particular named bacterial promoters include lacI, lacZ, T3, T7, gpt, lambda $P_R$, $P_L$ and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, a french press, mechanical disruption, or use of cell lysing agents, such methods are well know to those skilled in the art. However, preferred are host cells which secrete the polypeptide of the invention and permit recovery of the polypeptide from the culture media.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and/or purified from recombinant cell cultures by well-known protein recovery and purification methods. Such methodology may include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. In this respect, chaperones may be used in such a refolding procedure. Finally, high performance liquid chromatography (HPLC) can be employed for final purification steps.

The polypeptides that are useful as immunogens in the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

Procedures for the isolation of the individually expressed polypeptides may be isolated by recombinant expression/isolation methods that are well-known in the art. Typical examples for such isolation may utilize an antibody to a conserved area of the protein or to a His tag or cleavable leader or tail that is expressed as part of the protein structure.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The invention will be further described with respect to the following examples; however, the scope of the invention is not limited thereby:

EXAMPLE 1

Active Protection with Anti-Sp36

A. Cloning, Expression, and Purification of SP36

The genomic DNA used as target for amplification was isolated from *S. pneumoniae* Norway strain (serotype 4), the same strain used for genomic sequencing. The complete sequence of the Sp36 gene (SEQ ID NO:9), and its predicted amino acid sequence (SEQ ID NO:8), are given in the Sequence Listing appended hereto. It was noted that the predicted amino acid sequence included a hydrophobic leader sequence followed by a sequence (LSVC-SEQ ID NO: 13) similar to the consensus sequence for Type II signal peptidase (LxxC (SEQ ID NO: 14)), in which both x's typically represent small amino acids). Primers (listed as SEQ ID NOS:1–3) were designed that would amplify the Sp36 gene and allow its cloning into pQE10 and expression as a histidine-tagged protein lacking the signal sequence for purification by nickel-affinity chromatography. Cloning of the fragment amplified by SEQ ID Nos 1 and 3 would result in a protein containing amino acids 21 through 819 of Sp36; cloning of the fragment amplified by SEQ ID Nos 2 and 3 would result in a protein containing amino acids 26 through 819 of Sp36 (amino acid numbers refer to SEQ ID NO:8).

B. Active Protection with Sp36 Vaccination

In each of the three experiments shown in FIGS. 1A–1C, C3H/HeJ mice (10/group) were immunized intraperitoneally (i.p.) with Sp36 protein (15 µg in 50 µl PBS emulsified in 50 µl complete Freund's adjuvant (CFA)). A group of 10 sham-immunized mice received PBS with adjuvant. A second immunization of 15 µg protein with incomplete Freund's adjuvant (IFA) was administered 4 weeks later; the sham group received PBS with IFA. Blood was drawn (retro-orbital bleed) at weeks 3, 6, and 9; and sera from each group were pooled for analysis of anti-Sp36 antibody by ELISA. Mice were challenged at week 10 by an i.p. injection of approximately 500 CFU *S. pneumoniae* strain SJ2 (serotype 6B; provided by P. Flynn, St. Jude Children's Research Hospital, Memphis, Tenn.). In preliminary experiments, the $LD_{50}$ of this strain was determined to be approximately 10 CFU. Mice were monitored for 14 days for survival.

The three experiments shown in FIGS. 1A–1C used slightly different preparations of recombinant Sp36. The experiments shown in FIGS. 1A and 1B both used Sp36 containing amino acids 20–815, but different batches of protein were used in the two experiments. The experiment shown in FIG. 1C used Sp36 containing amino acids 25–815.

In the experiment shown in FIG. 1A, 9-week sera collected from the ten mice immunized with Sp36 (first batch) had an endpoint ELISA titer of 1:4,096,000. No anti-Sp36 antibody was detected in sera from sham-immunized mice. One hundred percent of the mice immunized with Sp36 protein survived the challenge (520 cfu of pneumococci) for 14 days. Eighty percent of sham-immunized mice were dead by day 4, and the remainder survived.

In the experiment shown in FIG. 1B, 9-week sera collected from the ten mice immunized with Sp36 (second batch) had an endpoint ELISA titer of >1:4,096,000. No anti-Sp36 antibody was detected in sera from sham-immunized mice. One hundred percent of the mice immunized with Sp36 protein survived the challenge (510 cfu of pneumococci) for 14 days. Of the sham-immunized mice, eighty percent were dead by day 4, and all died by day 9.

In the experiment shown in FIG. 1C, 9-week sera collected from the ten mice immunized with Sp36 (containing amino acids 25–815) had an endpoint ELISA titer of 1:4,096,000. No anti-Sp36 antibody was detected in sera from sham-immunized mice. One hundred percent of the mice immunized with Sp36 protein survived the challenge (510 cfu of pneumococci) for 14 days. Of the sham-immunized mice, ninety percent died by day 4, and all died by day 12. These data demonstrate that immunization of mice with recombinant Sp36 proteins elicits a response capable of protecting against systemic pneumococcal infection and death. This protection was not strain-specific: the recombinant pneumococcal protein was cloned from a serotype 4 strain, while the challenge was with a heterologous strain, SJ2 (serotype 6B).

EXAMPLE 2

Passive Protection with Anti-Sp36 Antisera

A. Generation of Rabbit Immune Sera

Following collection of preimmune serum, a New Zealand White rabbit was immunized with 250 µg of Sp36 (containing amino acids 20–815) in CFA. The rabbit was given two boosts of 125 µg Sp36 in IFA on days 29 and 50 and bled on days 39 and 60. A second rabbit was immunized with a control antigen, *E. coli* FimC.

B. Passive Protection in Mice

Figure 2:
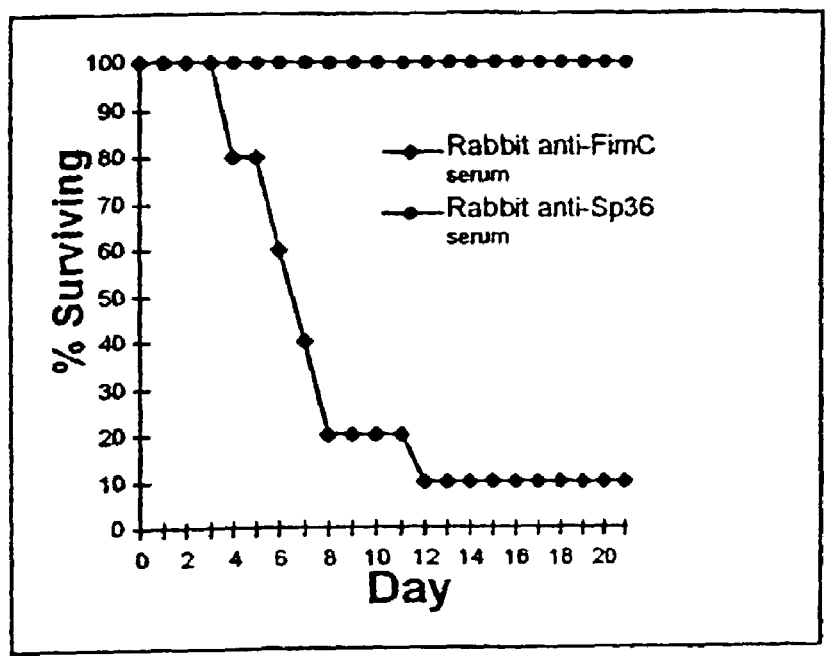
FIGS. 2A–2B show that passive administration of rabbit antiserum raised against Sp36 derived from Norway type 4 was able to protect mice in the pneumococcal sepsis model using two heterologous strains.
Figure 2:
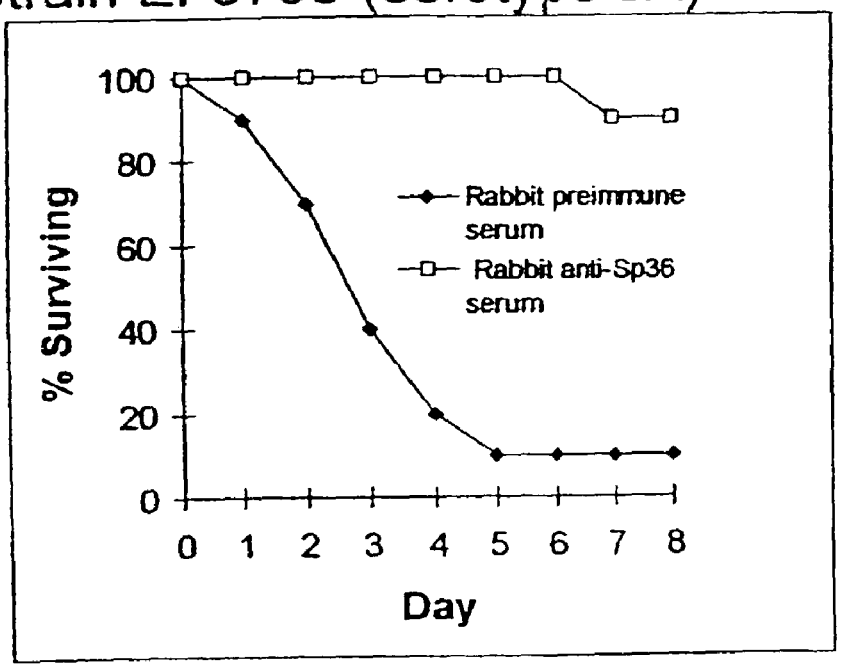

C3H/HeJ mice (10 mice/group) were passively immunized by two i.p. injections of 100 µl of rabbit serum. The first injection was administered twenty-four hours before challenge with 172 cfu of *S. pneumoniae* strain SJ2, and the second injection was given four hours after challenge. FIG. 2 shows the survival of mice after infection with two different strains of pneumococci.

FIG. 2A shows that of mice injected with 172 cfu of strain SJ2 (FIG. 2A), one hundred percent of the mice immunized with rabbit immune serum raised against Sp36 protein survived the 21-day observation period. Of the mice immunized with the control serum (anti-FimC), eighty percent died by day 8, and ninety percent died by day 12. FIG. 2B shows that of mice injected with 862 cfu of strain EF6796, ninety percent of the mice immunized with rabbit immune serum raised against Sp36 protein survived the 8-day observation period. Of those given a control serum (collected from a rabbit before immunization), ninety percent died by day 8.

These data indicate that the protection against pneumococcal infection resulting from immunization with Sp36 is antibody-mediated, since mice can be protected by passive transfer of serum from a hyperimmunized rabbit. As seen in the mouse active challenge experiments described above, serum directed against recombinant Sp36 protein cloned from a serotype 4 strain was protective against challenge with heterologous strains.

EXAMPLE 3

Conservation of Sp36 Among Strains of *S. pneumoniae*

A. Western Blotting

The 23 pneumococcal strains used in this experiment were obtained from the American Type Culture Collection (Rockville, Md.) and include one isolate each of the 23 serotypes in the multivalent pneumococcal vaccine. For total cell lysates, pneumococci were grown to mid-logarithmic phase (optical density at 620 nm, 0.4 to 0.6) in 2 ml Todd-Hewitt broth with 0.5% yeast extract (Difco, Detroit, Me.) at 37° C. Bacteria were harvested by centrifugation and washed twice with water. Pellets were resuspended in 200 μl lysis buffer (0.01% sodium dodecyl sulfate, 0.15 M sodium citrate and 0.1% sodium deoxycholate) and incubated at 37° C. for 30 min, then diluted in an equal volume 2×SSC (0.3 M sodium chloride, 0.03 M sodium citrate). Lysates were separated by SDS-PAGE, transferred to nitrocellulose membranes (Bio-Rad Laboratories, Hercules, Calif.), and probed with antibody in a standard Western blotting procedure. Sera from ten C3H/HeJ mice immunized with Sp36 (as described in Example 1) were pooled and used at a dilution of 1:3000. Bound antibody was detected with peroxidase-conjugated sheep anti-mouse IgG using the chemiluminescence kit from Amersham, Inc. (Cambridge, Mass.).

Figure 3A:
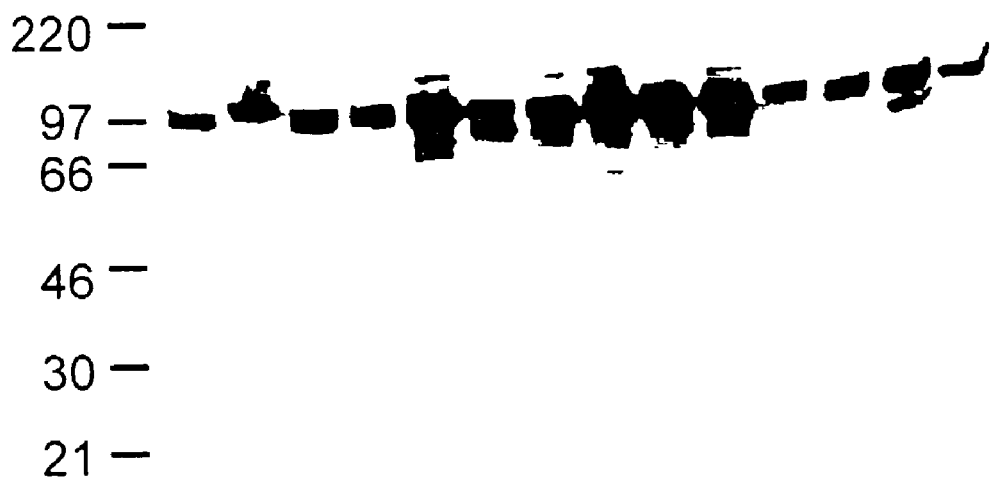
FIG. 3 is a western blot demonstrating the ability of antisera raised against recombinant Sp36 derived from strain Norway type 4 to react with Sp36 of heterologous strains. Total cell lysates were immunoblotted with mouse antisera to Sp36. A band representing Sp36 protein was detected in all 23 *S. pneumoniae* strains tested, which included isolates from each of the 23 pneumococcal serotypes represented in the current polysaccharide vaccine.
Figure 3B:
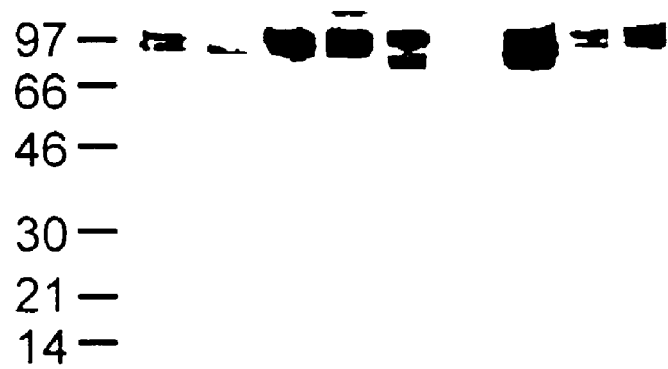

The mouse anti-Sp36 sera detected two major bands with apparent molecular weights of 97 and 100 kDa in all 23 pneumococcal lysates tested (shown in FIG. 3). The Sp36 signals obtained from *S. pneumoniae* serotypes 1, 5, 17F and 22F were lower, indicating either that the level of Sp36 expression is reduced in these strains, or that Sp36 in these strains is antigenically different.

These data show that Sp36 is antigenically conserved among strains of the 23 pneumococcal serotypes represented in the current polysaccharide vaccine.

B. Southern Blotting

Figure 4:
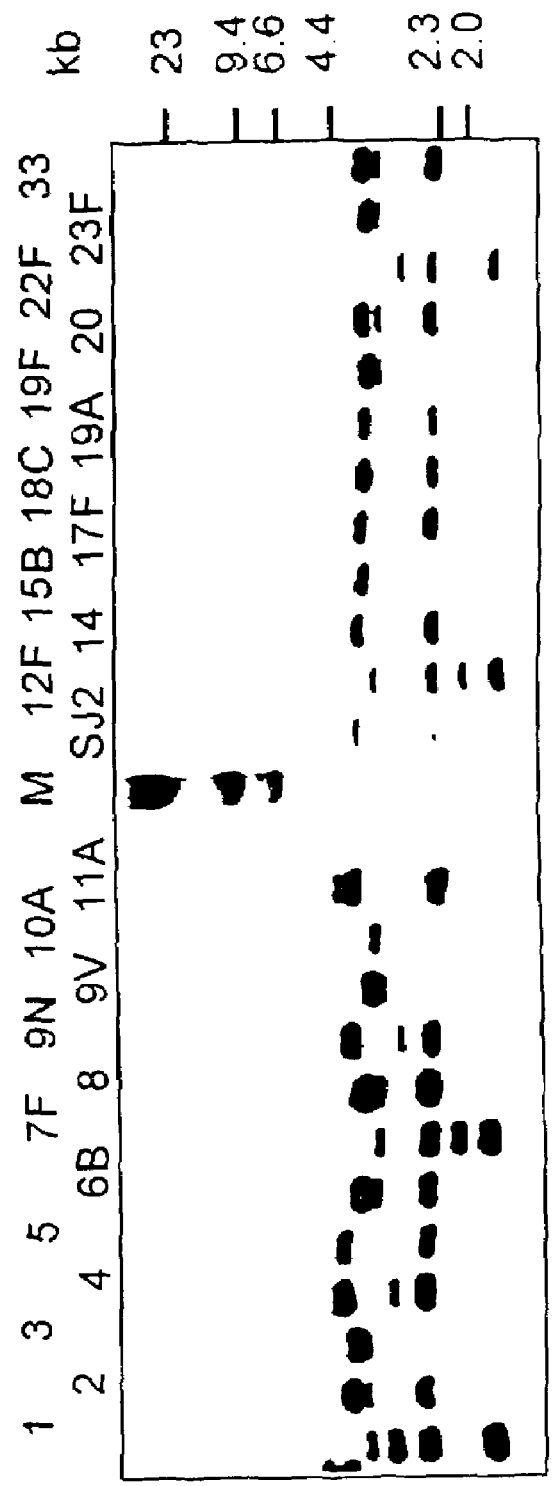
FIG. 4 is a Southern blot showing that the Sp36 gene from Norway type 4 hybridizes with genomic DNA from 24 other pneumococcal strains, indicating the presence of similar sequences in all these strains.

Genomic DNA was prepared from each of the 23 pneumococcal strains listed in the previous section and also from strain SJ2. DNA was digested with PvuII and BamHI, electrophoresed in an agarose gel and transferred to a nylon membrane. A probe was prepared by amplifying the Sp36 gene from Norway type 4 DNA (as in Example 1) and labeling the amplified fragment with fluorescein by the random-priming method, using a kit from Amersham. Hybridization, washing, and exposure of film were carried out as in the protocol supplied by Amersham. FIG. 4 shows that the Sp36 probe hybridized with DNA from each of the 24 strains studied. The lane marked "M" contained DNA from lambda phage, digested with HindIII and labeled with fluorescein, as molecular weight markers.

EXAMPLE 4

Immunogenicity of Sp36 in Humans

Figure 5A:
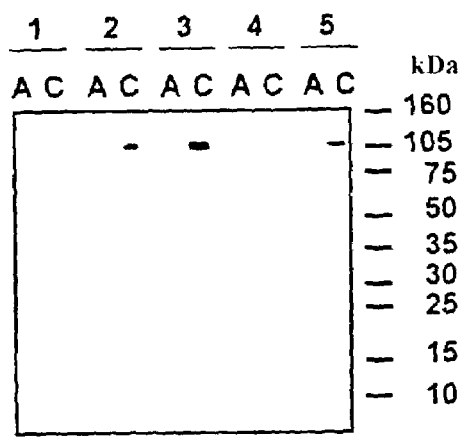
FIG. 5 is a western blot showing the reactivity of patient sera with Sp36. Sp36 (either full-length, panel A; N-terminal half, panel B; or C-terminal half, panel C) was electrophoresed by SDS-PAGE and transferred to nitrocellulose. Patient sera collected soon after the onset of illness (acute serum, lanes A) or eight to 30 days later (convalescent serum, lanes C) were used to probe the blots. For patients 2, 3, and 5, convalescent serum reacted more strongly with Sp36 than did the corresponding acute serum.
Figure 5B:
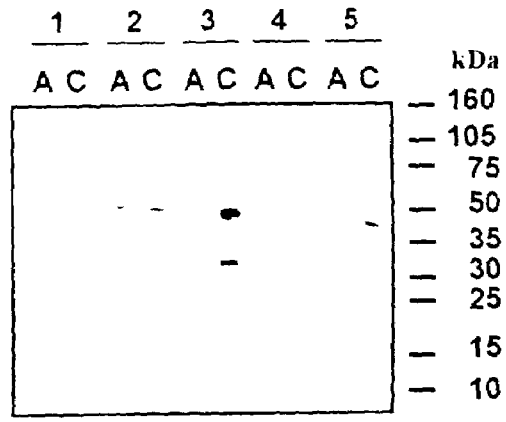
Figure 5C:
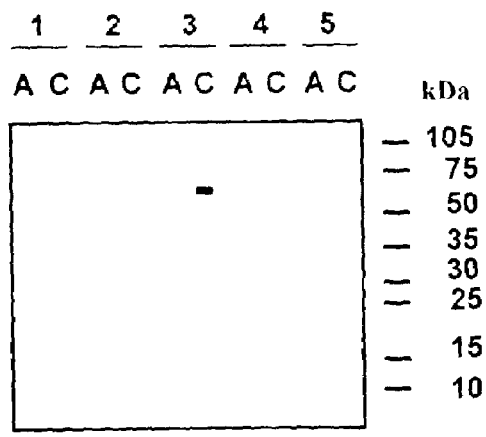

In order to determine whether Sp36 is immunogenic during human pneumococcal infection, sera from patients with culture-proven pneumococcal bacteremia were used in Western blots containing recombinant Sp36 protein. In the experiment shown in FIG. 5, sera from five patients (indicated as 1 through 5) were diluted 1:3000 and used to probe blots containing full-length Sp36, the N-terminal half of Sp36 (preceding the proline-rich region), or the C-terminal half of Sp36 (following the proline-rich region). Lanes labeled A (acute) were probed with serum collected shortly after diagnosis of pneumococcal infection; lanes C (convalescent) were probed with serum collected either one month later (patients 1, 2, and 3) or eight days after the first serum collection (patients 4 and 5). For patients 2, 3 and 5, reactivity of the convalescent serum with Sp36 was stronger that that of the corresponding acute serum. The difference between the acute and convalescent sera was particularly evident for reactivity with the C-terminal half of the protein.

In additional experiments (not shown), convalescent sera from 23 patients with pneumococcal infections were tested individually for reactivity with full-length Sp36: 20 of the 23 sera were found to bind Sp36 on a Western blot.

These experiments indicate that Sp36 is recognized by the human immune system and suggest that antibodies able to bind the Sp36 protein may be produced during natural *S. pneumoniae* infection in humans. Since the patients were infected with a variety of pneumococcal strains, these data also support the idea that Sp36 is antigenically conserved.

EXAMPLE 5

Table 1 provides the percent identity between the various sequences.

Alignment of the predicted amino acid sequences of PhtA, PhtB, PhtD, and PhtE using the MEGALIGN program of Lasergene showed strong N-terminal homology with substantial divergence of the C-termini (FIG. 6). The alignment of the nucleotide sequences of the same genes is shown in FIG. 7. Amino acid and nucleotide sequences were compared using the identity weighting in a Lipman-Pearson pairwise alignment, in which the number of matching residues is divided by the total of matching residues plus the number of mismatched residues plus the number of residues in gaps. In the table below, the percent identity between each pair of sequences is shown at the intersection of the corresponding row and column.

EXAMPLE 6

Active Protection with PhtD Vaccination

Figure 8:
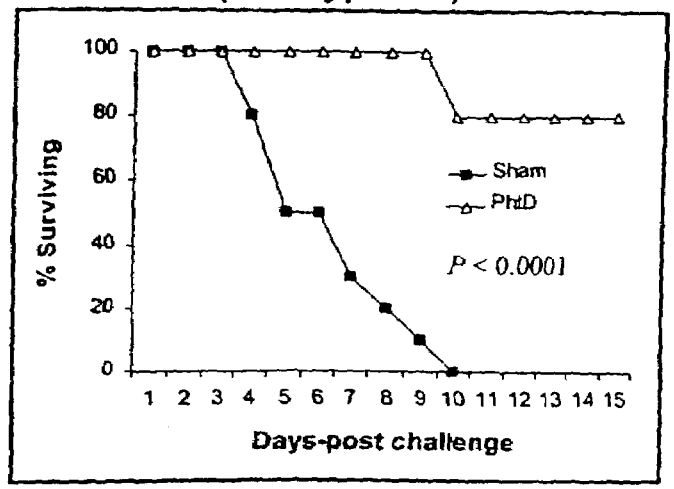
FIG. 8 shows the results of immunization of mice with PhtD recombinant protein, which leads to protection from lethal sepsis. C3H/HeJ (Panel A and B) or Balb/cByJ (Panel C) mice were immunized subcutaneously with PhtD protein (15 µg in 50 µl PBS emulsified in 50 µl complete Freund's adjuvant (CFA)). The recombinant PhtD protein used in protection experiments consisted of 819 amino acid residues, starting with the cysteine (residue 20). A group of 10 sham-immunized mice received PBS with adjuvant. A second immunization of 15 µg protein with incomplete Freund's adjuvant (IFA) was administered 3 weeks later; the sham group received PBS with IFA. Blood was drawn (retro-orbital bleed) at week 7; and sera from each group was pooled for analysis of anti-PhtD antibody by ELISA. Mice were challenged at week 8 by an intraperitonial (i.p.) injection of approximately 550 CFU *S. pneumoniae* strain SJ2, serotype 6B (Panel A), 850 CFU of strain EF6796, serotype 6A (Panel B) or 450 CFU of strain EF5668, serotype 4 (Panel C). In preliminary experiments, the $LD_{50}$ for strain SJ2 and EF6796 were determined to be approximately 10 CFU for both strains. The $LD_{50}$ for strain EF5668 was determined to be <5 CFU. Survival was determined in all groups over the course of 15 days following challenge. Data are presented as the percent survival for a total of 10 mice per experimental group. Two-sample Log-rank test was used for statistical analysis comparing recombinant Pht immunized mice to sham-immunized mice.
Figure 8:
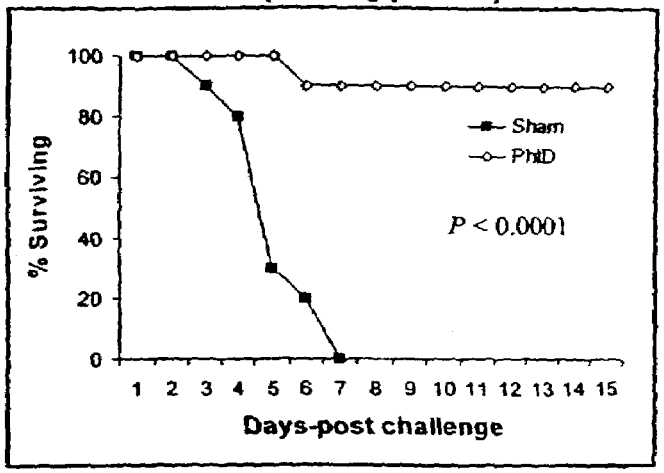
Figure 8:
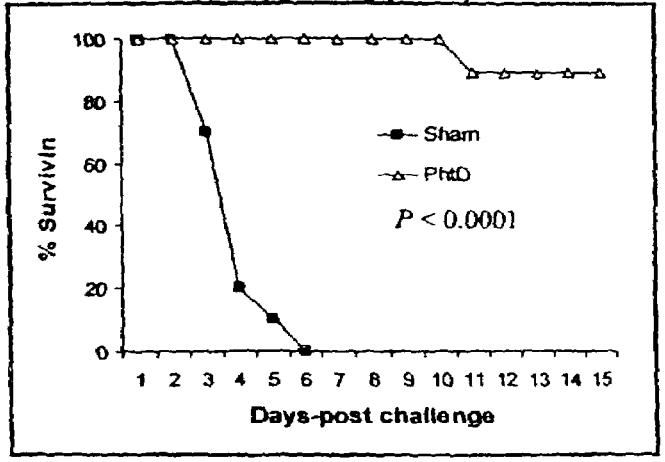

Mice immunized with recombinant PhtD derived from strain N4 generated potent antibody titers (reciprocal end-point titers ranging from 2,048,00 to 4,096,000). Mice immunized with PhtD were protected against death following intraperitoneal injection with either of three heterologous strains, SJ2 (serotype 6B; provided by P. Flynn, St. Jude Children's Research Hospital, Memphis, TN), EF6796 (serotype 6A) or EF5668 (serotype 4; both strains provided by D. Briles, University of Alabama, Birmingham). In the experiment shown in FIG. 8 (Panel A), all ten of the sham-immunized mice died within 10-days after challenge with virulent pneumococci (strain SJ2), while eighty percent of the PhtD-immunized mice survived the 15-day observation period. Immunization with PhtD also protected against a serotype 6A strain, EF6796 (Panel B) and a serotype 4 strain, EF5668 (Panel C). In the experiment shown in FIG. 8 (Panel B), all ten of the sham-immunized mice died within 7-days after challenge with virulent pneumococci (strain EF6796), while ninety percent of the PhtD-immunized mice survived the 15-day observation period. In the experiment shown in FIG. 8 (Panel C), all ten of the sham-immunized mice died within 6-days after challenge with virulent pneumoccoci (strain EF5668), while eight of nine mice immunized with PhtD survived the 15-day observation period.

TABLE 1

Percent Identities

|  | PhtA | PhtB | PhtD | PhtE |
|---|---|---|---|---|
| Percent Identity Between Amino Acid Sequences ||||
| PhtA | — | 66.4 | 63.9 | 49.5 |
| PhtB |  | — | 87.2 | 49.5 |
| PhtD |  |  | — | 49.8 |
| PhtE |  |  |  | — |
| Percent Identity Between Nucleotide Sequences ||||
| PhtA | — | 58.3 | 59.3 | 47.9 |
| PhtB |  | — | 86.4 | 47.4 |
| PhtD |  |  | — | 47.9 |
| PhtE |  |  |  | — |

What is claimed is:

1. A method for eliciting an immune response to *Streptococcus pneumoniae* in a mammal comprising administering to said mammal an isolated polypeptide comprising an amino acid sequence that has at least 95% identity to amino acids 20–838 of SEQ ID NO: 4.

2. The method of claim 1 wherein said percent identity is at least 97%.

3. The method of claim 1 wherein said isolated polypeptide comprises the amino acid sequence of SEQ ID NO: 4.

4. A method for eliciting an immune response to *Streptococcus pneumoniae* in a mammal comprising administering to said mammal an isolated polypeptide comprising an active fragment of amino acids 20–838 of SEQ ID NO: 4 wherein said active fragment comprises at least two coiled coil regions.

5. The method of claim 4 wherein said active fragment comprises at least one histidine triad region.

6. The method of claim 4 wherein said active fragment comprises at least two histidine triad regions.

7. The method of claim 4 wherein said active fragment comprises at least three histidine triad regions.

8. The method of claim 1 wherein said polypeptide is administered in a pharmaceutically acceptable carrier.

9. The method of claim 4 wherein said active fragment is administered in a pharmaceutically acceptable carrier.

10. A method for eliciting an immune response to *Streptococcus pneumoniae* in a mouse comprising administering to said mouse an isolated polypeptide comprising an amino acid sequence that has at least 95% identity to amino acids 20–838 of SEQ ID NO: 4.

* * * * *